(12) United States Patent
Rafiee et al.

(10) Patent No.: US 12,691,259 B2
(45) Date of Patent: *Jul. 28, 2026

(54) TISSUE CUTTING SYSTEMS AND METHODS

(71) Applicants: Telltale LLC, Andover, MA (US); The National Institutes of Health (NIH), Bethseda, MD (US)

(72) Inventors: Nasser Rafiee, Andover, MA (US); Robert J Lederman, Bethseda, MD (US); Rany Busold, Andover, MA (US); Morgan House, Andover, MA (US); Jaffar Khan, Bethseda, MD (US); Toby Rogers, Bethseda, MD (US); Christopher G Bruce, Bethseda, MD (US)

(73) Assignees: TellTale LLC, Andover, MA (US); The National Institutes of Health (NIH), Bethseda (MD)

( * ) Notice: Subject to any disclaimer, the term of this patent is extended or adjusted under 35 U.S.C. 154(b) by 1018 days.

This patent is subject to a terminal disclaimer.

(21) Appl. No.: 17/710,149

(22) Filed: Mar. 31, 2022

(65) Prior Publication Data

US 2022/0288357 A1 Sep. 15, 2022

Related U.S. Application Data

(63) Continuation-in-part of application No. 17/148,170, filed on Jan. 13, 2021, now Pat. No. 11,337,753,
(Continued)

(51) Int. Cl.
| | |
|---|---|
| *A61M 25/09* | (2006.01) |
| *A61B 90/00* | (2016.01) |
| *A61M 25/01* | (2006.01) |

(52) U.S. Cl.
CPC ............. *A61M 25/09* (2013.01); *A61B 90/39* (2016.02); *A61M 25/0108* (2013.01); *A61M 2025/09166* (2013.01); *A61M 2025/09175* (2013.01)

(58) Field of Classification Search
CPC ......... A61M 2025/09108; A61M 2025/09166; B23P 27/00; B23P 27/02
See application file for complete search history.

(56) References Cited

U.S. PATENT DOCUMENTS

| | | | |
|---|---|---|---|
| 4,493,320 | A | 1/1985 | Treat |
| 5,417,697 | A | 5/1995 | Wilk et al. |

(Continued)

FOREIGN PATENT DOCUMENTS

| | | |
|---|---|---|
| DE | 10037660 A1 | 2/2002 |
| DE | 202010016945 U1 | 3/2011 |

(Continued)

OTHER PUBLICATIONS

Written Opinion mailed Jan. 27, 2022 for International Patent Application No. PCT/US2021/049952.
(Continued)

*Primary Examiner* — Ronald Hupczey, Jr.
(74) *Attorney, Agent, or Firm* — DeWitt LLP; Brian R. Pollack, Esq.

(57) ABSTRACT

The disclosure provides various embodiments of systems to facilitate the cutting of luminal tissue structures percutaneously.

10 Claims, 23 Drawing Sheets

Related U.S. Application Data which is a continuation-in-part of application No. PCT/US2020/055160, filed on Oct. 9, 2020, application No. 17/710,149 is a continuation of application No. PCT/US2021/049952, filed on Sep. 10, 2021, and a continuation-in-part of application No. 17/148,616, filed on Jan. 14, 2021, now abandoned.

(60) Provisional application No. 63/047,995, filed on Jul. 3, 2020, provisional application No. 63/077,579, filed on Sep. 12, 2020.

(56) References Cited

U.S. PATENT DOCUMENTS

| | | | | |
|---|---|---|---|---|
| 5,599,300 | A * | 2/1997 | Weaver | A61B 18/1492 |
| | | | | 128/898 |
| 5,807,279 | A | 9/1998 | Viera | |
| 6,017,340 | A | 1/2000 | Cassidy et al. | |
| 6,050,995 | A | 4/2000 | Durgin | |
| 6,501,992 | B1 | 12/2002 | Belden et al. | |
| 6,517,551 | B1 | 2/2003 | Driskill | |
| 6,533,782 | B2 | 3/2003 | Howell et al. | |
| 6,582,425 | B2 | 6/2003 | Simpson | |
| 6,695,836 | B1 * | 2/2004 | DeMello | A61B 18/1492 |
| | | | | 606/29 |
| 7,160,295 | B1 | 1/2007 | Garito et al. | |
| 7,303,798 | B2 | 12/2007 | Bavaro et al. | |
| 7,455,646 | B2 * | 11/2008 | Richardson | A61M 25/09 |
| | | | | 600/585 |
| 8,827,948 | B2 | 9/2014 | Romo et al. | |
| 9,282,993 | B1 | 3/2016 | Cohen et al. | |
| 9,572,666 | B2 | 2/2017 | Basude et al. | |
| 9,833,272 | B2 | 12/2017 | Sweeney | |
| 9,980,716 | B2 | 5/2018 | Harris et al. | |
| 11,337,753 | B2 * | 5/2022 | Rafiee | A61B 90/39 |
| 2003/0088195 | A1 * | 5/2003 | Vardi | A61B 5/1076 |
| | | | | 600/585 |
| 2004/0267161 | A1 * | 12/2004 | Osborne | A61L 31/10 |
| | | | | 600/585 |
| 2005/0171532 | A1 | 8/2005 | Ciarocca | |
| 2007/0293857 | A1 | 12/2007 | Blind et al. | |
| 2008/0228209 | A1 | 9/2008 | DeMello et al. | |
| 2009/0005637 | A1 | 1/2009 | Chin et al. | |
| 2012/0123328 | A1 | 5/2012 | Williams | |
| 2014/0276605 | A1 | 9/2014 | Tejani et al. | |
| 2017/0007277 | A1 | 1/2017 | Drapeau et al. | |
| 2018/0008268 | A1 * | 1/2018 | Khairkhahan | A61B 18/1492 |
| 2019/0175199 | A1 | 6/2019 | Girdhar et al. | |
| 2019/0298521 | A1 | 10/2019 | Rafiee et al. | |
| 2020/0001053 | A1 | 1/2020 | Rafiee | |
| 2020/0383717 | A1 | 12/2020 | Lederman et al. | |

FOREIGN PATENT DOCUMENTS

| | | | |
|---|---|---|---|
| EP | 3175813 | B1 | 1/2020 |
| RU | 2152757 | C1 | 7/2000 |
| WO | WO 99/51149 | A1 | 10/1999 |
| WO | 2018009718 | A1 | 1/2018 |
| WO | 2019/040943 | A1 | 2/2019 |
| WO | 2019164806 | A1 | 8/2019 |
| WO | 2021072331 | A1 | 4/2021 |

OTHER PUBLICATIONS

International Search Report mailed Jan. 27, 2022 for International Patent Application No. PCT/US2021/049952.
Unpublished International Patent Application No. PCT/US2021/049952 downloaded from ePCT on Jan. 28, 2022.
Written Opinion of the International Searching Authority for International Application No. PCT/US2018/048177 mailed Nov. 19, 2018.
International Search Report for International Application No. PCT/US2018/048177 mailed Dec. 20, 2018.
Khan et al., "Intentional Laceration of the Anterior Mitral Valve Leaflet to Prevent Left Ventricular Outflow Tract Obstruction During Transcatheter Mitral Valve Replacement", JACC: Cardiovascular Interventions vol. 9, No. 17, 2016.
Babaliaros et al., "Intentional Percutaneous Laceration of the Anterior Mitral Leaflet to Prevent Outflow Obstruction During Transcatheter Mitral Valve Replacement First-in-Human Experience", JACC: Cardiovascular Interventions vol. 10 , No. 8, 2017.
Lederman et al., "Preventing Coronary Obstruction During Transcatheter Aortic Valve Replacement From Computed Tomography to Basilica", JACC: Cardiovascular Interventions vol. 12 , No. 13. 2019, pp. 1197-1216.
Khan et al., "Predicting Left Ventricular Outflow Tract Obstruction Despite Anterior Mitral Leaflet Resection The "Skirt NeoLVOT"", JACC: Cardiovascular Interventions Sep. 2019, vol. 11 , No. 9, pp. 1356-1359.
Case, "Tip to Base Lampoon to PRevent Left Ventricular Outflow Tract Obstruction in Valve in Valve Transcatheter Mitral Valve Replacement", JACC: Cardiovascular Interventions, May 2020, vol. 13, No. 9, pp. 1126-1128.
Greenbaum et al., "First-in-human transcatheter pledglet-assisted suture tricuspid annuloplasty for severe tricuspid insufficiency," Catheterization and Cardiovascular Interventions, May 2020, 5 pages.
Kamioka et al., "Bi-Silica During Transcatheter Aortic Valve Replacement for Noncalcific Aortic Insufficiency: Initial Human Experience", JACC: Cardiovascular Interventions, Nov., 2018, vol. 11, No. 21, pp. 2237-2239.
Kasel et al, "International Lampoon: First European experience with laceration of the anterior mitral valve leaflet prior to transseptal transcatheter mitral valve implantation", Eurointervention, Sep. 2018, col. 14, No. 7, pp. 746-749.
Khan et al, "The Basilica Trial: Prospective Multicenter Investigation of Intentional Leaflet Laceration to Prevent TAVR Coronary Obstruction", JACC: Cardiovascular Interventions, 2019, vol. 12, No. 13, pp. 1240-1252.
Khan et al, "Transcatheter Mitral Valve Replacement after Transcatheter Electrosurgical Laceration of Alfieri stitch (Elastic): First in human report," JACC: Cardiovascular Interventions, Apr. 2018, vol. 11, No. 8, pp. 1808-1811.
Khan et al., "Transcatheter Electrosurgery: JACC State of the art review," Journal of the American College of Cardiology, Mar. 2020, vol. 75, No. 12, pp. 1455-1470.
Khan et al., "Anterior Leaflet Laceration to Prevent Ventricular Outflow Tract Obstruction During Transcatheter Mitral Valve Replacement," Journal of the American College of Cardiology, May 2019, vol. 73, No. 20, pp. 2521-2534.
Khan et al, "Rescue Lampoon to Treat Transcatheter Mitral Valve Replacement—Associated Left Ventricular Outflow Tract Obstruction", JACC: Cardiovascular Interventions, Jul. 2019, vol. 12, No. 13, pp. 1283-1284.
Lisko et al., "Pachyderm Shape guiding catheters to simplify Basilica leaflet traversal," Cardiovsacular Revascularization Medicine, Sep. 2019, vol. 20, No. 9, pp. 782-785.
Lisko et al., "Electrosurgical detachment of Mitraclips from the anterior mitral leaflet prior to transcatheter mitral valve implantation," JACC: Cardiovascular Interventions, Oct. 2020, vol. 13, No. 20, pp. 2361-2370.
Khan et al., "Lampoon to facilitate tendyn Anterior Leaflet Laceration to Prevent Ventricular Outflow Tract Obstruction During Transcatehter Mitral Valve Replacement," Journal of the American College of Cardiology, May 2019, vol. 73, No. 20, pp. 2521-2534.
Written Opinion and International Search Report mailed Mar. 1, 2021 for International Patent Application No. PCT/US2020/055160.
Written Opinion and International Search Report mailed Oct. 22, 2021 for International Patent Application No. PCT/US2021/040511.
Extended European Search Report for Application No. 18848165.9 dated Apr. 30, 2021.
Supplementary European Search Report and European Search Opinion for Application No. 19756527.8 dated Oct. 18, 2021.

(56)　　　　　　　　References Cited

OTHER PUBLICATIONS

Supplementary European Search Report for EP Application No. 21867713.6, dated Sep. 17, 2024, 9 pages.
Israeli Office Action dated Jul. 30, 2025, 4 pages.

* cited by examiner

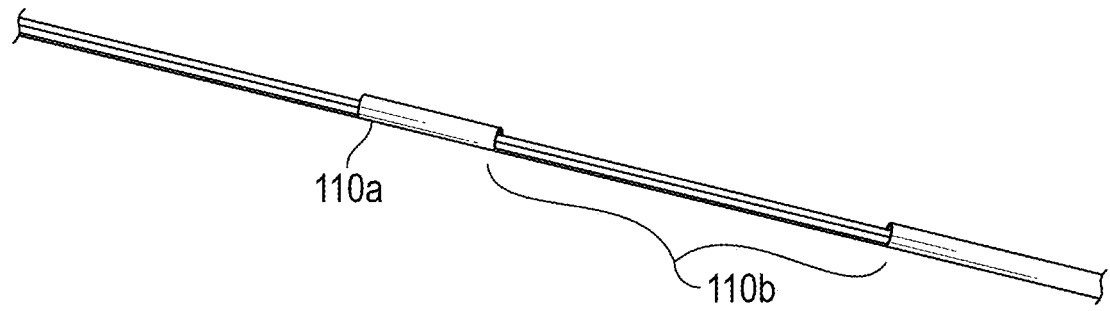
FIG. 4
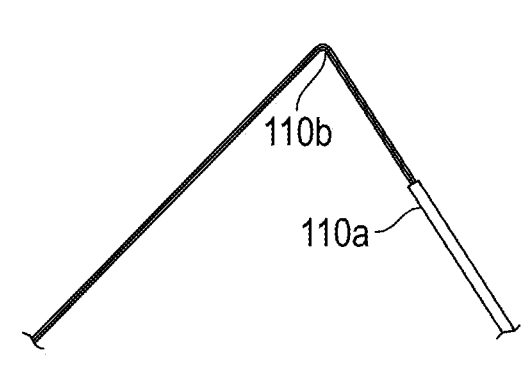
FIG. 5
FIG. 6

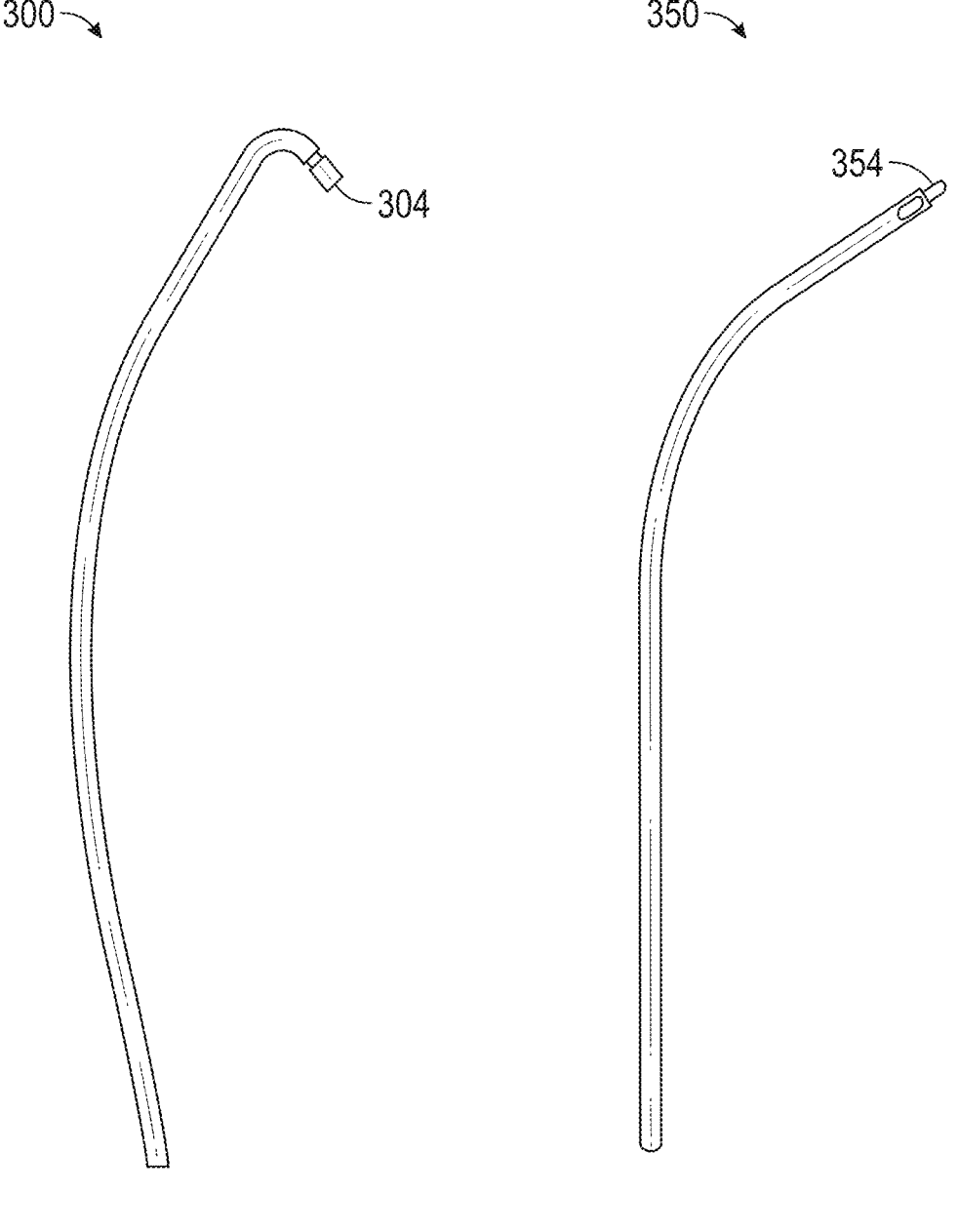
300
304
350
354
FIG. 10                    FIG. 11

700

710

745

755    722

712    730

724

100

740

720

712

745  720d

748

710          720c

720b

720a

727

TISSUE CUTTING SYSTEMS AND METHODS

CROSS-REFERENCE TO RELATED APPLICATION

The present patent application claims the benefit of priority to International Patent Application No. PCT/US21/49952, filed Sep. 10, 2021, which in turn claims the benefit of priority to U.S. patent application Ser. No. 17/148,616, filed Jan. 14, 2021, U.S. patent application Ser. No. 17/148,170, filed Jan. 13, 2021, U.S. Patent Application No. 63/077,579, filed Sep. 12, 2020 and International Patent Application No. PCT/US2020/055160, filed Oct. 9, 2020. This patent application also claims the benefit of priority to U.S. patent application Ser. No. 17/148,170, filed Jan. 13, 2021, which in turn claims the benefit of priority to U.S. Patent Application No. 63/047,995, filed Jul. 3, 2020, U.S. Patent Application No. 63/077,579, filed Sep. 12, 2020 and International Patent Application No. PCT/US2020/055160, filed Oct. 9, 2020.

FEDERALLY-SPONSORED RESEARCH AND DEVELOPMENT

This invention was made with Government support under contract no. HHSN268201800017C awarded by the National Institutes of Health. The U.S. Government has certain rights in the invention.

BACKGROUND

The disclosure relates generally to medical treatment devices and techniques, and, in some aspects, to methods and devices for diagnosis and treatment of cardiac valves. The present disclosure provides improvements over the state of the art.

SUMMARY OF THE DISCLOSURE

Heart valve leaflets can obstruct desired blood flow in some circumstances, such as when a leaflet is pushed into an open position by the implantation of a prosthetic heart valve within another. The present disclosure provides solutions to avoid such obstructions.

Disclosed are implementations of tissue cutters and related devices that can be used to lacerate valve leaflets. The wires can include a wire that is at least partially covered by electrical insulation. Devices are provided to form a kink in the wire that defines an inner curvature. The wire can be exposed through the insulation at one or more exposed regions along or near the inner curvature of the kink. The wire can be coupled to an electrosurgical system and a supporting catheter system to facilitate the application of electrical energy through the exposed region(s) and through a tissue target positioned adjacent the inner curvature to cut the tissue target via the electrical energy. The tissue target can be a native or prosthetic heart valve leaflet in a patient's heart.

In some implementations, an irrigation catheter can also be used to inject a non-ionic liquid adjacent to the exposed portions of the cutter to displace blood and reduce with electrical dissipation. The disclosed cutters can be used in various methods disclosed herein to cut heart valve leaflets within the heart, including, for example, at the aortic valve, mitral valve, tricuspid valve, and pulmonary valve, as well as other types of tissue structures. Cutting valve leaflets can help prevent or reduce problems associated with the leaflets blocking desired blood flow, especially when a prosthetic heart valve is implanted within a native heart valve, or within another prosthetic heart valve.

In some implementations, the disclosure provides an electrosurgical guidewire. The electrosurgical guidewire includes a core wire having a proximal end, and a distal end and is defined by an outer surface between the proximal end and the distal end of the core wire. The core wire is defined by a centerline that traverses the length of the core wire from the proximal end to the distal end of the core wire.

In some implementations, the guidewire includes a radiopaque marker pattern, or pattern of one or more radiopaque markers, disposed over the core wire to indicate a location proximate a middle section of the guidewire to be kinked and used to cut through tissue during an electrosurgical procedure. A dielectric coating can disposed (e.g. deposited, coated, and the like) at least partially about the core wire and the radiopaque marker pattern. The proximal end and distal end of the core wire can be exposed and the proximal end of the guidewire can be configured to be coupled to an electrosurgical generator. The dielectric coating can be configured to be stripped from the guidewire proximate the radiopaque marker pattern.

In some implementations, the radiopaque marker pattern can define a central region to be crimped and stripped of the dielectric coating, and one or more indicia on either side of the central region. The indicia can be used for purposes of measurement when conducting a medical procedure.

In various embodiments, the radiopaque marker pattern can include a radiopaque metallic material. If desired, the radiopaque marker pattern can include gold metallic material deposited over the core wire. If desired, the radiopaque marker pattern can include gold metallic material electroplated on the core wire using a mask to form the marker pattern. The radiopaque marker pattern can include an uneven or roughened surface configured to enhance its visual signature under fluoroscopy.

In some implementations, the radiopaque indicia can include a plurality of spaced marker bands disposed on either side of the central region of the radiopaque marker pattern. If desired, the central region of the radiopaque marker pattern can be between about 0.5 cm and 2 cm in length and each of the plurality of spaced marker bands can be between about 0.5 mm and 5 mm in length. In some implementations, the central region of the radiopaque marker pattern can be about 1 cm in length and each of the plurality of spaced marker bands can be about 1 mm in length, wherein each marking can be separated by a gap, for example, of about 1 mm.

In some implementations, the dielectric material can have a dielectric strength at 1 mil thickness between about 5600 V/mil and 7500 V/mil. The dielectric material can be any suitable dielectric material, such as a polymeric coating and the like. In some implementations, the dielectric coating is formed in whole or in part from parylene, such as parylene C. Alternatively, parylene N can be used. The parylene can be deposited over the core wire and the radiopaque marker pattern by way of any suitable technique, such as chemical vapor deposition, for example.

In various embodiments, the guidewire can have different dimensions and thicknesses. In some embodiments, the guidewire has an outside diameter of about 0.014 inches, including the thickness of radiopaque markers and coatings. The dielectric material coating can have a thickness between about 0.1 mil and about 20 mil, for example, or any increment therebetween of about 0.1 mil.

In various implementations, the core wire can include at least one section of reduced diameter in the region of the radiopaque marker pattern. For example, the region of the core wire in the region of the radiopaque marker pattern can be ground down to provide a recessed region to accommodate the radiopaque marker pattern. This can be done to maintain the profile of the guidewire along its length. The radiopaque marker pattern can have a thickness, for example, between about 0.0005 inches and about 0.0010 inches, or any increment therebetween of 0.0001 inches. If desired, a radiopaque coil can surround the distal tip of the guidewire.

The disclosure further provides implementations of an electrosurgical system. The system includes an electrosurgical generator, and a pair of guiding catheters, each guiding catheter having a proximal end and a distal end and defining an elongate lumen along its length. The system further includes a guidewire as set forth herein that is kinked and electrically exposed in the central region of the radiopaque marker pattern. Each of the guiding catheters is disposed over a portion of the guidewire between the kinked central region of the radiopaque marker pattern and the proximal and distal ends of the core wire. The proximal end of the core wire is coupled to the electrosurgical generator. A distal end of each said guiding catheter is spaced from the kinked portion of the core wire by aligning the distal end of each guiding catheter with measurement indicia disposed on either side of the kinked portion of the core wire to space the distal end of each guiding catheter from the electrically exposed portion of the core wire in order to prevent the guiding catheters from being damaged by current flowing across the electrically exposed portion of the core wire.

If desired, implementations of the electrosurgical system can further include a gripper coupled to a proximal end of each guiding catheter. Each gripper is configured to be selectively coupled to the guidewire to permit the relative position of the guidewire and the guiding catheters to be fixed. The disclosure further provides a kit to perform an electrosurgical procedure, including a guidewire as set forth herein, guiding catheters as set forth herein, and, grippers as set forth herein, and a crimper to crimp and denude the core wire in the central region of the radiopaque marker pattern.

In some implementations, the kinker can include a first arm and a second arm joined at a rotatable hinge. The kinker can be configured to hold the electrosurgical guidewire in place with respect to the first arm and second arm to permit the electrosurgical guidewire to be kinked when the first arm and second arm are folded at the rotatable hinge. The kinker can include visual indicia thereon to provide alignment with the radiopaque marker pattern of the electrosurgical guidewire. The kinker can include an optical lens to magnify the radiopaque marker pattern of the electrosurgical guidewire. If desired, the kinker can include a rotatably mounted blade configured to be rotated about a central axis. Revolution of the rotatably mounted blade can strip the dielectric coating from the electrosurgical guidewire.

Methods of performing a valve leaflet cutting procedure are set forth herein. An illustrative method includes coupling a proximal end of an electrosurgical guidewire as set forth herein to an electrosurgical generator, directing a distal end of the electrosurgical guidewire into the patient's vasculature to a valve leaflet to be cut, energizing the electrosurgical generator to energize the distal exposed end of the electrosurgical guidewire, and burning the valve leaflet tissue to form an opening therethrough. The method can further include advancing the electrosurgical guidewire through the valve leaflet, capturing the distal end of the electrosurgical guidewire with a catheter configured to function as a snare catheter, and pulling the distal end of the guidewire out of the patient to externalize it alongside a proximal region of the electrosurgical guidewire.

If desired, the method can further include directing a guiding catheter over each portion of the externalized guidewire until a distal tip of each guiding catheter is located proximate the valve leaflet. The method can further include kinking and denuding the central region of the radiopaque marker pattern using the kinker while outside of the patient and advancing the kinked, denuded portion of the guidewire into the patient's anatomy until the kinked portion of the guidewire straddles the opening burned in the valve leaflet.

In some implementations, the valve leaflet can be punctured at a position located radially inwardly from a valve annulus. This is sometimes needed to as to avoid the need for puncturing the valve leaflet too close to the valve annulus where calcified deposits may have accumulated. Once the leaflet has been so punctured by a guidewire as set forth herein, a catheter including an inflatable member, such as a balloon, or other expansible catheter can be introduced over the guidewire and introduced through the hole in the leaflet. The inflatable member can then be expanded to enlarge the opening in the leaflet at least partially along a radially outward direction toward the valve annulus.

The distal tip of each guiding catheter can be advanced under visualization to a location proximal to the kinked denuded region of the guidewire, and indicia on the guidewire can be used to maintain a predetermined spacing between the guiding catheters and the kinked denuded region of the guidewire to prevent damage to the guiding catheters.

The method can further include activating the electrosurgical power source, and burning through the tissue of the valve leaflet using the kinked denuded portion of the guidewire to complete a cut through the valve leaflet.

The foregoing and other features and advantages of the disclosed technology will become more apparent from the following detailed description of several embodiments which proceeds with reference to the accompanying figures.

BRIEF DESCRIPTION OF THE FIGURES

FIGS. 4-6 illustrate further aspects of the guidewire of FIG. 1 in accordance with the disclosure.

FIGS. 8A-8C illustrate aspects of a first guide catheter in accordance with the present disclosure and an example of its use.

FIGS. 9A-9C illustrate aspects of a second guide catheter in accordance with the present disclosure and an example of its use.

FIGS. 10 and 11 are illustrations of profiles of guide catheters that can be configured to function as snare catheters in accordance with the present disclosure.

FIG. 23A demonstrates the direction of rotation of the knob to drag the cutting blade over the guidewire to remove the insulating layer from the guidewire.

FIG. 23B illustrates a cross section of the device as the blade removes the insulating material from the guidewire.

FIGS. 24A-24B illustrate views of the kinker after the cutter has reached its ending position.

FIG. 25A illustrates kinking of the guidewire by folding over the lens portion of the kinker about a pivot axis.

FIG. 25B illustrates a cross sectional view showing the blade in a stowed position to permit kinking of the guidewire placing the blade in a location away from the guidewire.

FIGS. 26A-26G illustrate aspects of a further representative embodiment of a gripper device in accordance with the present disclosure.

DETAILED DESCRIPTION

The present application presents advantages and improvements over systems described in U.S. patent application Ser. No. 16/954,710 ("the '710 application"), filed in the United States of America on Jun. 17, 2020. This patent application is incorporated by reference herein in its entirety for all purposes.

Applicant has come to appreciate that while the procedure set forth in the '710 application mentioned above is beneficial with respect to the mitral valve to prevent left ventricular outflow tract (LVOT) obstruction, the present disclosure provides specialized equipment that is far more useful as compared to the equipment to perform the procedure set forth in the '710 application. Moreover, the present disclosure adds the particular example of cutting leaflet(s) of the aortic valve so as to prevent obstruction of the coronary arteries. The disclosed embodiments make these types of procedures safer, faster, more consistent and predictable so as to make it a more practical therapeutic approach. It will be appreciated that the disclosed embodiments can be modified as needed to have appropriate geometry to cut leaflets of any cardiac valve or other appropriate tissue structure.

One key area of improvement in this system flows from providing a redesigned special purpose guidewire to act as a charge concentration device. This guidewire can be used reliably and consistently, particularly when used with special purpose supporting devices to denude, kink and support the guidewire within an electrosurgical system, as described below.

Thus, in some aspects, the disclosure provides an electrosurgical guidewire. The electrosurgical guidewire includes a core wire having a proximal end, and a distal end and is defined by an outer surface between the proximal end and the distal end of the core wire. The core wire is defined by a centerline that traverses the length of the core wire from the proximal end to the distal end of the core wire.

Figures 1, 2:
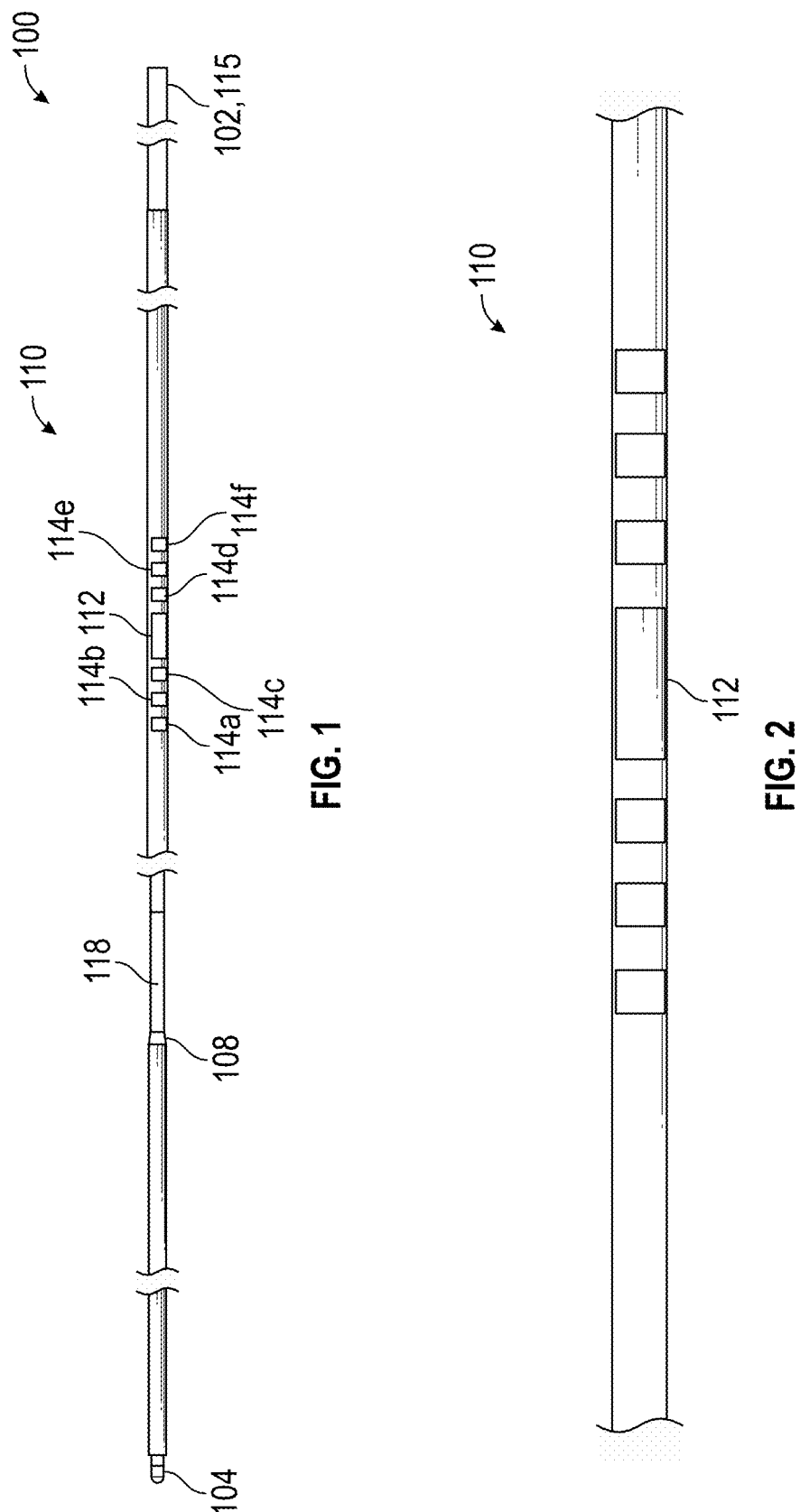
FIGS. 1-2 are illustrations of a guidewire in accordance with the present disclosure or aspects thereof.

For purposes of illustration, and not limitation, FIGS. 1 and 2 illustrate an example of a guidewire 100 having a proximal end 102 and a distal end 104. The guidewire 100 is built upon a core wire 115, such as of stainless steel that is ground down to match a desired profile. As illustrated, the guidewire includes a coating 118 along most of its length formed from an electrically insulating material, discussed in further detail below. As depicted, the proximal and distal ends 102, 104 of the guidewire are exposed to permit them to be coupled to an electrosurgical generator and/or be used to burn through tissue. The core wire 115 can be stainless steel (e.g., Hyten, SLT Type 4) for strength and maintaining straightness.

In some implementations, the guidewire 100 includes a radiopaque marker pattern 110, or pattern of one or more radiopaque markers, disposed over the core wire 115, and underneath the insulating coating 118, to indicate a location along the guidewire 100 proximate a middle section of the guidewire that is to be kinked and used to cut through tissue during an electrosurgical procedure, described in further detail below. The proximal end 102 and distal end 104 of the core wire 115 can be exposed and can be configured to be coupled to an electrosurgical generator. The dielectric coating 118 can be configured to be stripped from the guidewire proximate the radiopaque marker pattern, described in further detail below. The guidewire 100 can have a denuded tip or distal end 102, such as the last 1-5 mm or any increment of 0.1 mm therebetween, and a denuded proximal end 102 (e.g., 0.5-30 mm of length). The proximal denuded region is preferably roughened to enhance physical contact with the spring loaded connector 610 of cable 600. If desired, the marker pattern can be formed from a plurality of marker bands, or a single elongate marker section. To manufacture the guidewire with the markers, in some implementations, an elongate rod is ground down in the region where the marker(s) are to be located. Next, a radiopaque material, such as gold, platinum, or the like is deposited in the recesses formed by the grinding. Thereafter, the core wire can be plunge ground and shaped to its final diameter prior to coating with dielectric material and/or other coatings.

This provides a smooth continuous core wire surface along the length of the core wire including in the region(s) of the marker band(s).

In some implementations, the radiopaque marker pattern 100 can define a central region 112 to be crimped and stripped of the dielectric coating 118, and one or more indicia 114(*a-f*) on either side of the central region. The indicia can be used for purposes of measurement or determining relative distances when conducting a medical procedure.

In various embodiments, the radiopaque marker pattern 110 can include a radiopaque metallic material. In a preferred embodiment, the radiopaque marker pattern includes gold metallic material deposited over the core wire 115. If desired, the radiopaque marker pattern 110 can include gold metallic material electroplated on the core wire 115 using masking techniques to form the marker pattern 110.

The radiopaque marker pattern 110 can include an uneven or roughened surface configured to enhance its visual signature under fluoroscopy. The surface roughness can be achieved by various electroplating techniques. If desired, the surface roughness can have a roughness average between about 0.01 micrometers and about 100 micrometers or any increment therebetween of 0.01 micrometers, for example.

In some implementations, and as illustrated in FIG. 1, the radiopaque indicia 110 can include a plurality of spaced marker bands disposed on either side of a central marker band region 112 of the radiopaque marker pattern. For example, the central region of the radiopaque marker pattern 110 can be between about 0.5 cm and 2 cm in length and each of the plurality of spaced marker bands can be between about 0.5 mm and 5 mm in length. In the particular implementation of FIG. 2, the central region of the radiopaque marker pattern can be about 1 cm in length and each of the plurality of spaced marker bands can be about 1 mm in length, wherein each marking can be separated by a gap, for example, of about 1 mm. The longer center marker band (~1 cm) makes it more visible under fluoroscopy and to the naked eye. It helps a physician identify the mid-shaft of the guidewire 100 (where the marker is preferably located) and indicates the location to be denuded of insulation for the laceration portion of the procedure. The smaller marker bands on each side provide an easily identifiable pattern (e.g., "raccoon tail") under fluoroscopy and to naked eye. Such a unique pattern reduces confusion with other interventional device markers. Each 1 mm marker band, also allows physicians to measure how far the guide catheter tip is from the laceration surface of the guidewire.

In some implementations, the dielectric material used to form the insulating layer 118 can have a dielectric strength at 1 mil thickness between about 5600 V/mil and 7500 V/mil. The dielectric material can be any suitable dielectric material, such as a polymeric coating and the like. In some implementations, the dielectric coating is formed in whole or in part from parylene, such as parylene C. The parylene can be deposited over the core wire and the radiopaque marker pattern by way of any suitable technique, such as chemical vapor deposition, for example. The parylene coating is preferably transparent or translucent to permit visual identification of radiopaque marker pattern 110.

In various embodiments, the guidewire can have different dimensions and thicknesses. In some embodiments, the guidewire has an outside diameter of about 0.014 inches, including the thickness of radiopaque markers and coatings. The dielectric material coating can have a thickness between about 0.1 mil and about 20 mil, for example, or any increment therebetween of about 0.1 mil.

In various implementations, the core wire can include at least one section of reduced diameter in the region of the radiopaque marker pattern. For example, the region of the core wire 115 in the region of the radiopaque marker pattern 110 can be ground down to provide an elongate recessed region to accommodate the radiopaque marker pattern(s). This can be done to maintain the profile of the guidewire along its length and to ensure that its finished thickness including any coatings does not exceed 0.014 inches. The radiopaque marker pattern can have a thickness, for example, between about 0.0005 inches and about 0.0010 inches, or any increment therebetween of 0.0001 inches.

Figure 3:
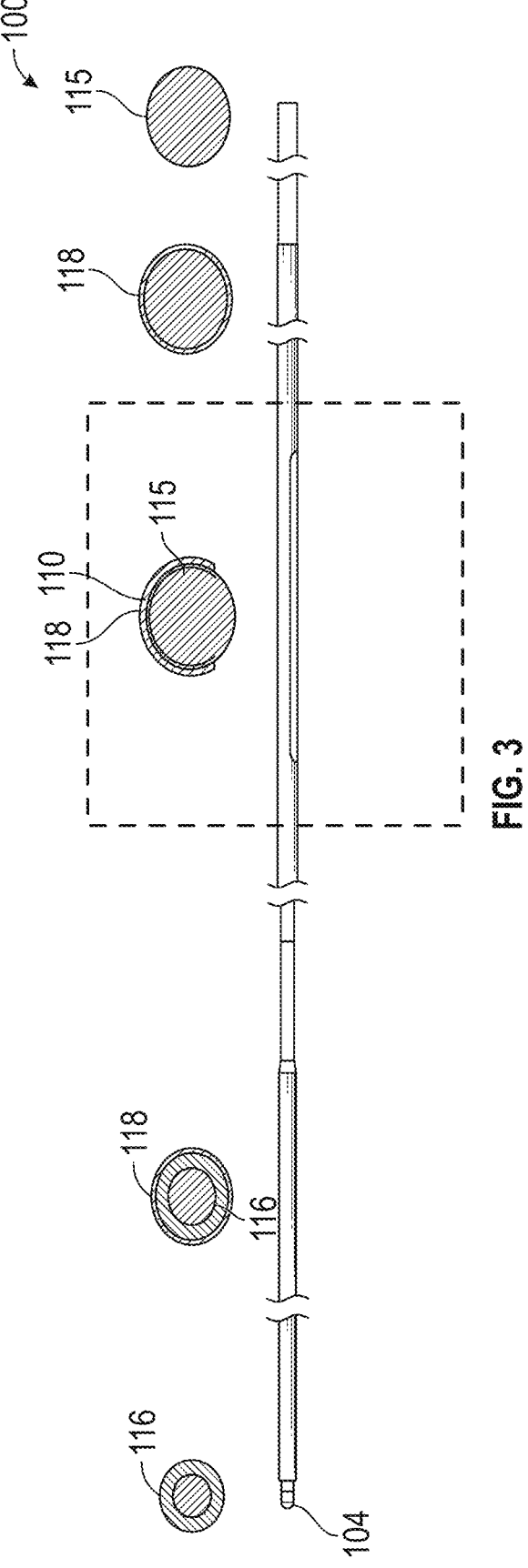
FIG. 3 is a schematic illustration of aspects of the guidewire of FIG. 1.

With reference to FIG. 3, if desired, a radiopaque coil 116 can surround the distal tip 104 of the guidewire 100 that is made from platinum or other suitable (and preferably radiopaque) material, such as a mixture of 90/10 platinum/iridium. FIG. 3 illustrates the relative placement of overlapping layers of material along the length of guidewire 100. With reference to the left, or distal, end of the guidewire 104, the core wire 115 is surrounded by coil 116. The spring coil can be laser welded to the core wire 115, for example, to withstand RF energy delivery therethrough. Immediately proximal to the distal end, layer 118 of insulating material begins, and extends to the proximal end of the guidewire at right. The central region of the guidewire is illustrated as having already been denuded of layer 118 and part of layer 110 using a denuder, as discussed below, to permit an electrosurgical procedure as set forth herein below to be carried out.

When denuding this region of the guidewire, typically about 3-5 mm of the guidewire is denuded. A small controlled denuded region allows for better concentration of energy to lacerate tissue and provides a steady cutting arc or plasma discharge. When denuded and kinked, the parylene coating and the gold-plated marker band underneath are scraped to reveal a "laceration" surface for which to delivery RF energy therethrough. Only the parylene coating needs to be denuded to deliver energy, but denuding the gold-plated marker band allows for visual confirmation of denudation because the coating is clear.

Figure 7:
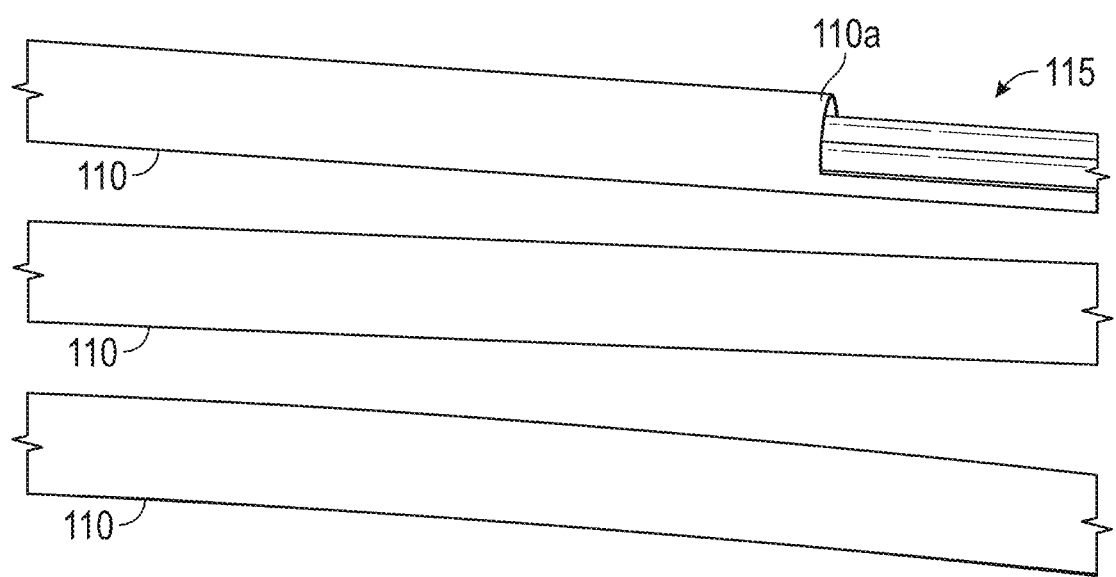
FIG. 7 is a close up view of the guidewire of FIG. 1 showing radiopaque material deposited on the guidewire.

FIG. 4 illustrates the guidewire 100 after it has been denuded along a region 110*b* to expose the core wire 115, prior to kinking. FIG. 5 illustrates the guidewire after it has been kinked, illustrating the relative placement of section 110*b* to locations 110*a* where the electroplated region of radiopaque material has ended. FIG. 6 illustrates the general shape of the kinked guidewire, which has been bent past 90 degrees to an acute angle. This permits some "spring" like behavior in the guidewire as the wire is bent further during the procedure to maintain a gap between the sections of wire. FIG. 7 presents an up close view of several such guidewires showing the roughened electroplated region (e.g., of gold) 110, and the location 110*a* where the electroplating ends, and the underlying material of the core wire 115 is exposed.

Figure 13:
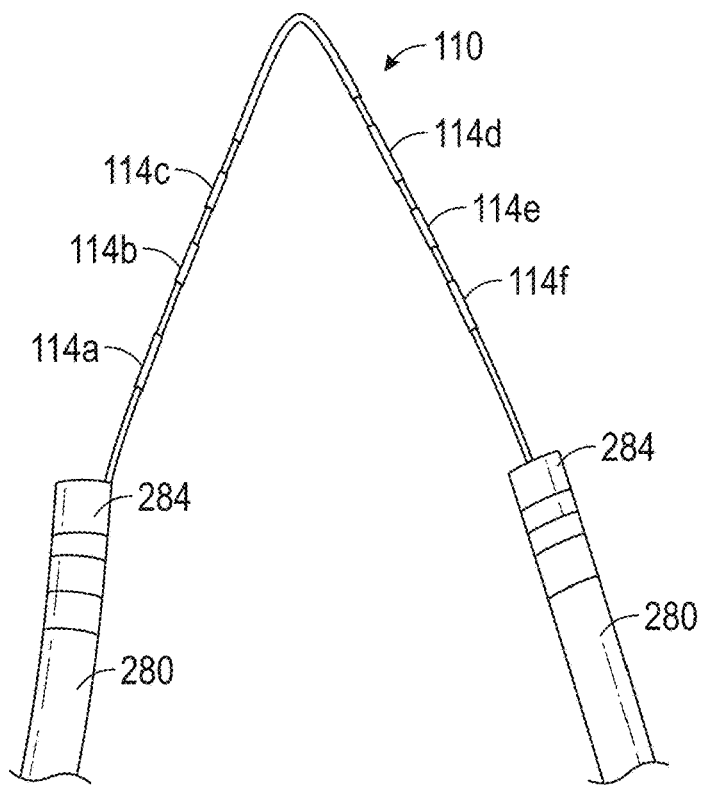
FIG. 13 is an illustration of a front end portion of an electrosurgical assembly including a crimped denuded guidewire supported by a pair of supporting guiding catheters in a position prior to cutting.
Figure 14:
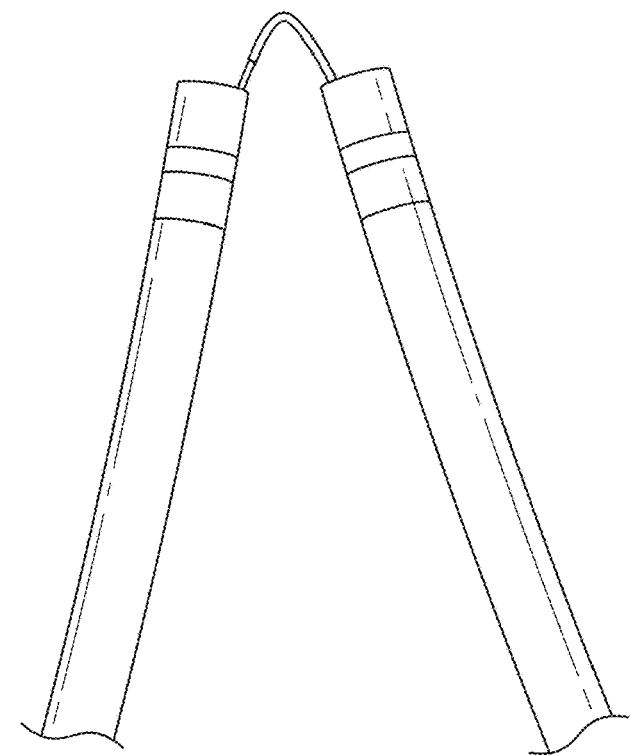
FIG. 14 is an illustration of a front end portion of an electrosurgical assembly including a crimped denuded guidewire supported by the pair of supporting catheters of FIG. 15 in a position when ready to cut.
Figure 15:
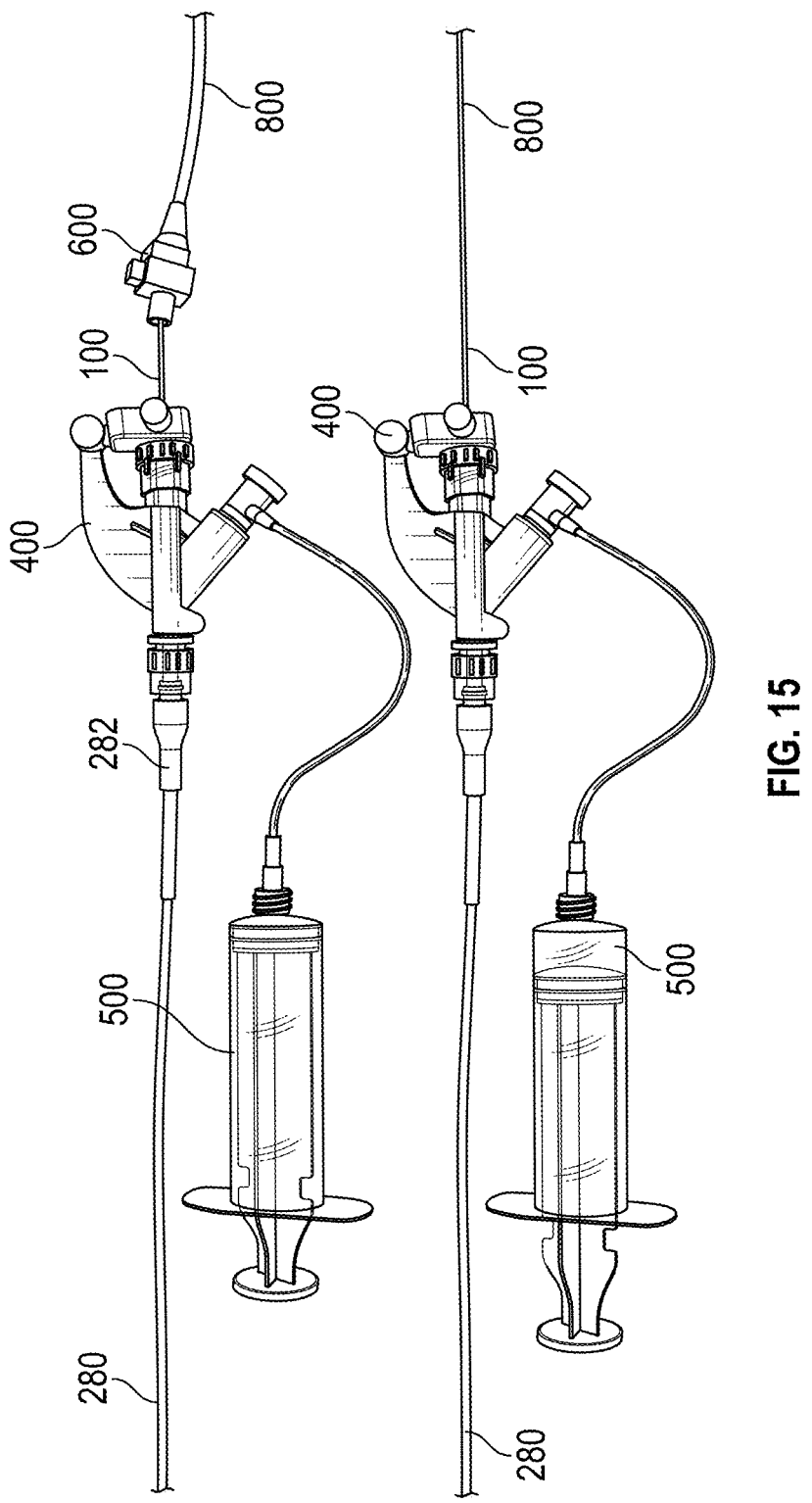
FIG. 15 is a depiction of a backend assembly of an electrosurgical system in accordance with the present disclosure showing a proximal end of the supporting or guiding catheters incorporated into the system.

The disclosure further provides implementations of an electrosurgical system. For purposes of illustration, and not limitation, FIGS. 13-15 illustrate aspects of such a system, including an electrosurgical generator 800 coupled to proximal end 102 of guidewire 100. The system further includes a pair of guiding catheters 280.

Figure 11A:
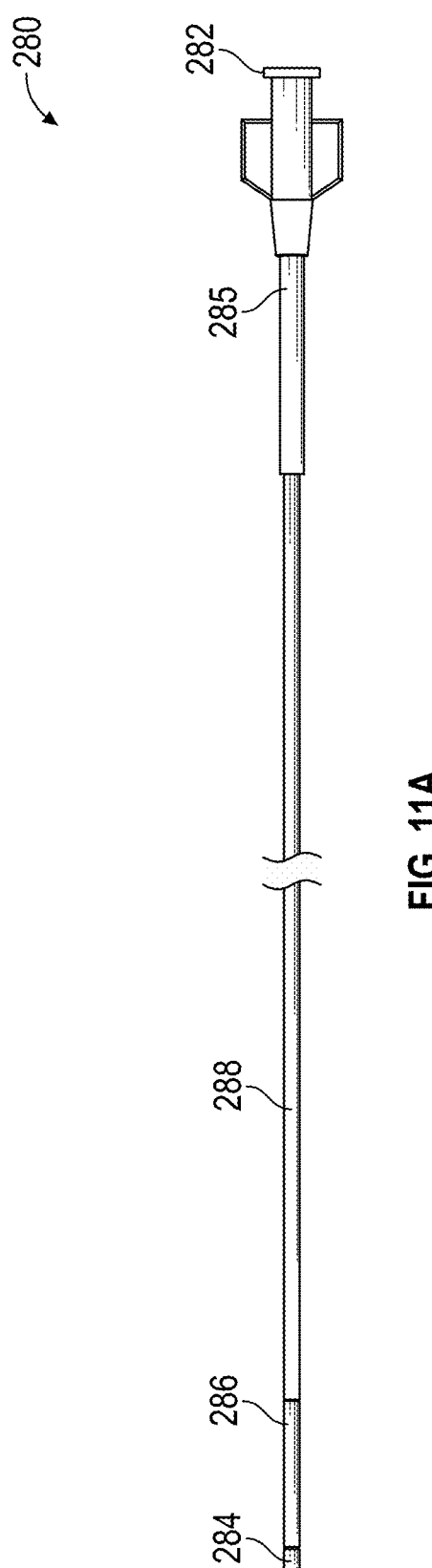
FIG. 11A is an illustration of aspects of a supporting or guiding catheter in accordance with the present disclosure.

With reference to FIG. 11A, each guiding or supporting catheter 280 has a proximal end 282 and a distal end 284 and defines an elongate lumen along its length. The proximal end 282 of the catheter includes a connector having a flange to couple to the proximal end 410 of gripper 400 as set forth in FIG. 15. The main body of the catheter 288 is formed by an elongate polymeric tube made, for example, from a high viscosity polyamide material, such as Vestamid ML21 (polyamide 12), having a Vicat softening temperature of 140 C according to ISO 306 and a Shore hardness of about 75 D, discussed in further detail below, and a length, L3, between 30 and 50 cm, for example. The main body 288 transitions to an intermediate region 286 near the distal end formed preferably from a material with a somewhat lower durometer, such as a polyether block amide (e.g., Pebax® elastomer) having a shore hardness form about 60 D to about 72 D and a relatively short length L2 of between 1 and 5 cm or any increment therebetween of 1 mm, such as a length of 2 cm. A distal tip portion of the catheter at location 284 can be made from a still softer material, such as Pebax material having a softness between 35 D and about 45 D, such as about 40 D. The distal tip portion can be short, having a length, L1, such as between 2 and 5 mm in length, such as 3 mm. Catheter 280 further can include a strain relief section 285 between, for example, 0.5 and 15 cm in length, to provide a transition in stiffness between the connector at the proximal end 282 of the catheter and the main body of the catheter 288. Sections 286, 288 can have a diameter, for example, between 0.08 and 0.09 inches, or any increment therebetween of 0.001 inches. The tip region 284 can have a diameter, for example, between 0.07 and 0.08 inches, or any increment therebetween of 0.001 inches. This basic configuration of catheter 280 can be shaped to form the other catheters disclosed herein, including catheters 200, 250, 300, and 350, depending on the valve being worked on in the procedure. Preferably, the catheters that are selected are used to deliver the guidewire 100, burn through the leaflet, and to retrieve and externalize the distal end 102 of the guidewire and perform the rest of the leaflet cutting procedure, as set forth herein.

Figure 27:
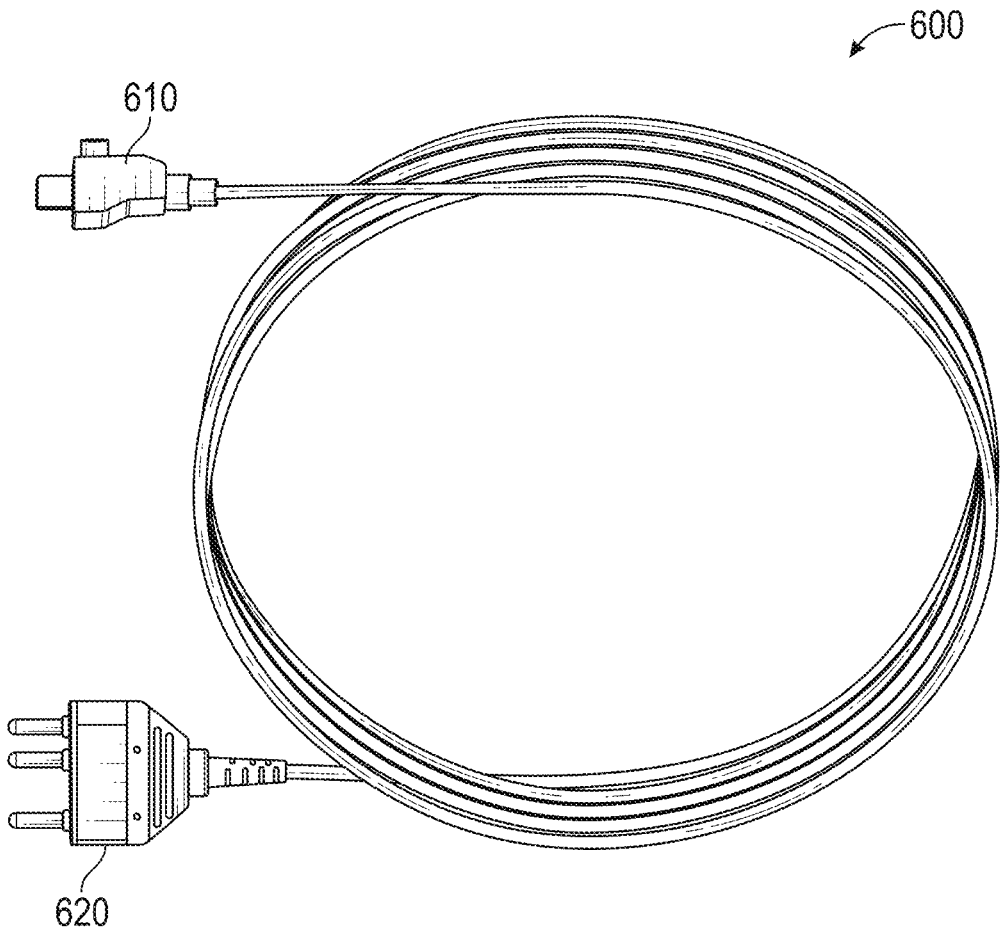
FIG. 27 depicts an electrical cable for use with a system as described in the present disclosure.

The system further includes a guidewire 100 as set forth herein that is kinked (FIGS. 13, 14) and electrically exposed in the central region of the radiopaque marker pattern 110. The guidewire 100 is placed with the kink therein straddling a valve leaflet using any of catheters 200, 250, 300, 350, as appropriate. Optionally, after this step, the opening in the valve leaflet can be enlarged with a balloon catheter as described elsewhere herein. The position of each of the guiding catheters is adjusted with respect to the guidewire 100 between the kinked central region 112 of the radiopaque marker pattern 100 and the proximal 102 and distal 104 ends of the guidewire. The proximal end of the core wire 115 is coupled to the electrosurgical generator 800 at least in part by way of a respective connector cable 600, shown in further detail in FIG. 27. Connector cable 600 includes a first end 610 with a spring loaded connector to connect to the proximal end 102 of the guidewire 100, and a second end having a plug 620 to connect to an electrosurgical generator, such as the Medtronic Force Triad and FT-10.

Figures 8A, 8B, 8C, 9A, 9B, 9C:
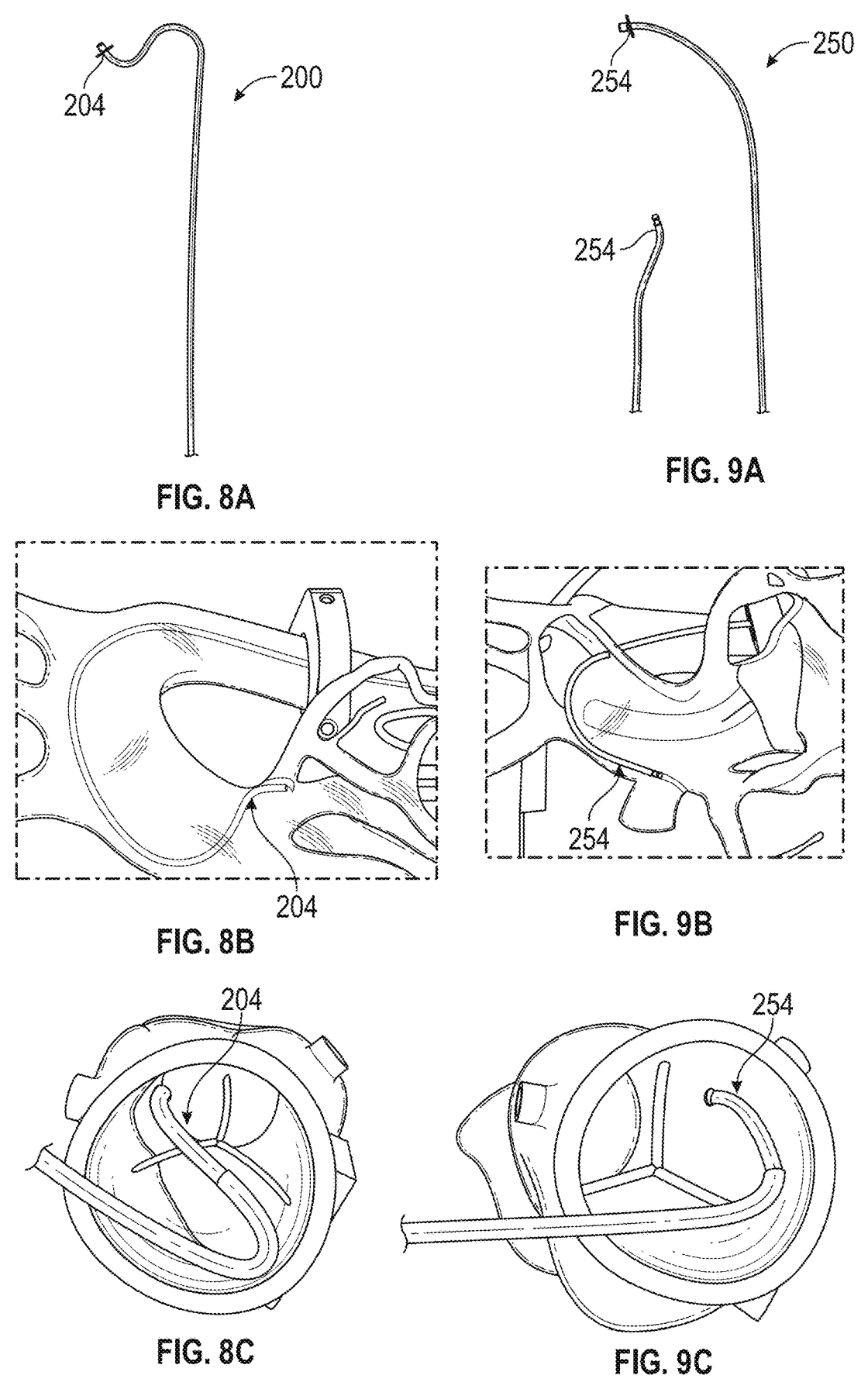

Catheter 280 from FIG. 11A can be shaped, for example, as catheter 200 in FIG. 8A, which is configured for approaching the left coronary cusp as shown in simulation on a model in FIGS. 8B and 8C. Suitable sizes can include PAL 0.75, PAL, 1.0 and PAL 2.0. The distal tip 204 rests in the left cusp and backup support is provided by the secondary curve of the catheter. The curve is stiff to avoid straightening during wire crossing through the leaflet. Similarly, catheter 280 from FIG. 11A can be shaped, for example, as catheter 250 in FIG. 9A, which is configured for approaching the right coronary cusp as shown in simulation on a model in FIGS. 9B and 9C. Distal tip 254 rests in the right cusp in FIG. 9C, and back up to maintain orientation is provided by bracing along the aortic arch wall. As mentioned above, once the guidewire 100 is in place to perform the cutting procedure, the position of these catheters is adjusted so as to avoid charring the tips of the catheters.

As set forth in FIGS. 13 and 14, distal end 284 of each said guiding catheter 280 is spaced from the kinked portion of the guide wire 100 by aligning the distal end 284 of each guiding catheter with measurement indicia 114a-f disposed on either side of the kinked portion of the wire 100 to space the distal end of each guiding catheter from the electrically exposed portion of the core wire in order to prevent the distal ends 284 of the guiding catheters 280 from being damaged by current flowing across the electrically exposed portion of the core wire 115.

The lumen of the guide catheters 280 are preferably large enough to deliver a flush of dextrose to prevent charring during energy delivery. Specifically, during the cutting operations, a dextrose solution is flushed through the catheters from reservoir 500 by way of conduits connecting to ports 440 in grippers 400. The flush can be manual. During the initial puncture of a leaflet, the flow rate of dextrose solution through the catheter 200/250 to the laceration location can be about 5 cc per second while the power to the guidewire is on. The flow rate of dextrose solution is preferably higher, such as 5-10 cc per second, during tissue laceration using the denuded section of guidewire.

If desired, and with continuing reference to FIG. 15, implementations of the electrosurgical system can further include a gripper 400 coupled to a proximal end of each guiding catheter 280.

For purposes of illustration, and not limitation, with reference to FIGS. 16 and 17, each gripper 400 can be configured to be selectively coupled to the guidewire 100 using a lock at the proximal end of the gripper 400, and to the supporting guiding catheter 280 at its distal end 410 to permit the relative position of the guidewire 100 and the distal ends 284 of the catheters 280 to be fixed. This helps to prevent the distal ends 284 of the guiding catheters from being melted.

Figure 16A:
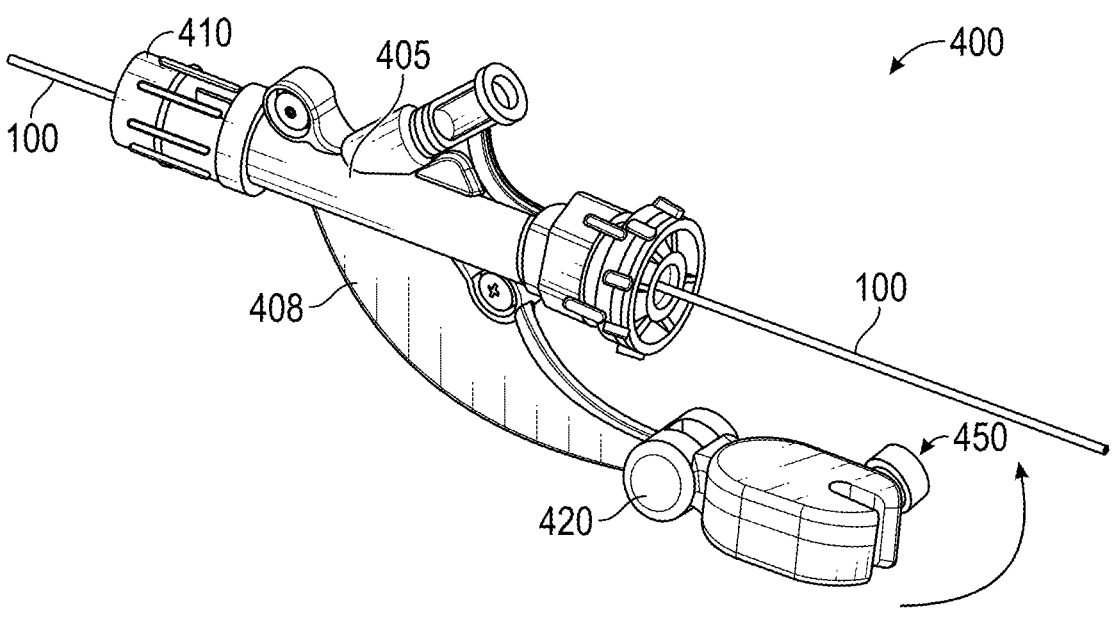
FIG. 16A is an isometric view of a guidewire gripper in an open position.
Figure 16B:
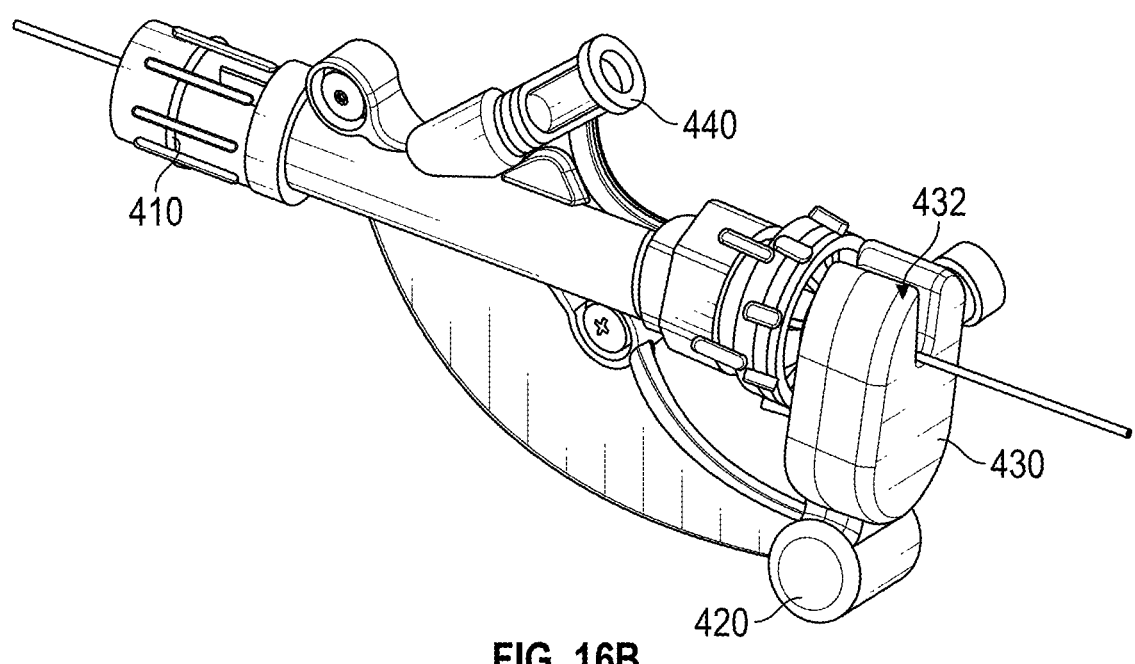
FIG. 16B is an isometric view of a guidewire gripper in a closed position.

As depicted in FIGS. 16A-16B, each gripper 400 is characterized by a main body 405 that defines a lumen therethrough (not shown) to permit passage of the guidewire 100. The main body includes a lock 410 at the distal end to engage a guide catheter, and a proximal end through which an end of the guidewire 100 extends. A port 440 such as for flushing fluid (e.g., dextrose solution) through the guide catheter is disposed on an upper side of the main body in a y-connector arrangement, and defines a lumen therethrough into the lumen defined along the length of the main body. A lower arm or wing 408 extends downwardly from the main body of the gripper 400 and terminates in a hinge 420, to which a rotatable arm 430 is mounted that in turn includes a clamp 450. The arm 430 is rotated about the hinge 420 and defines a groove 432 therethrough to receive the guidewire 100, where the guidewire is clamped in place, as discussed below.

To use the gripper, the wire is inserted through the lumen of the body 405 of the device. The arm 430 of the gripper is flipped up about hinge 420. The wire 100 falls into the channel 432 defined in the arm 430. The screw 450 is then tightened to advance the grip plate 452, which may also include a roughened surface that faces the wire 100, to hold the wire 100 in place. Grip plate 452 is adjacent a block 451, which may be formed from metal or plastic and contained within and held in place by housing or shell 455. Providing some vertical distance between screw 450 and screws 454 provides a sufficient distance for the plate 452 to bend about the point defined by screws 454 when screw 450 is tightened.

Figure 17A:
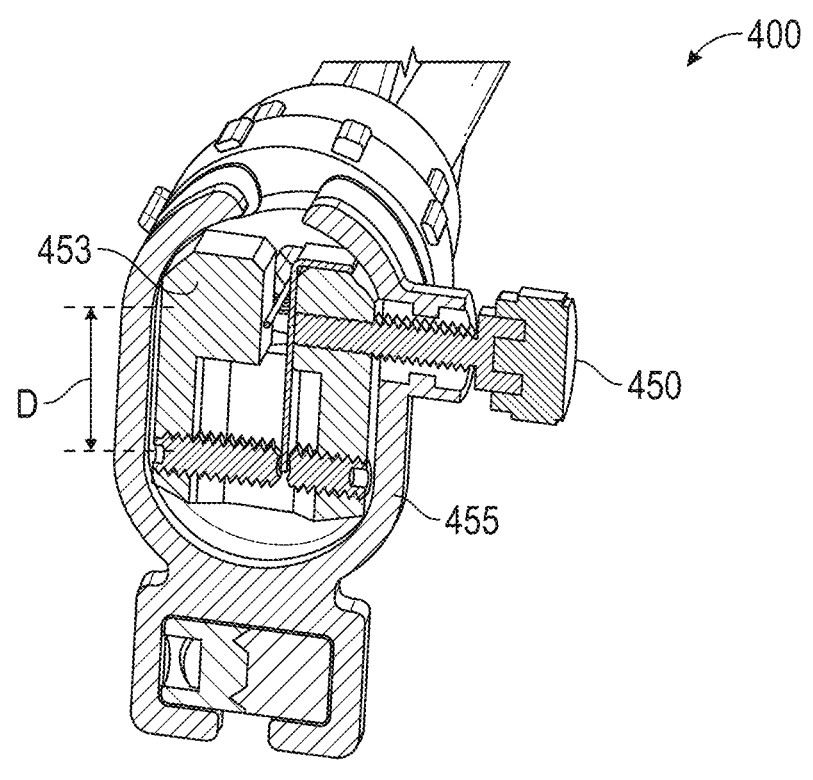
FIGS. 17A-17B are cross sectional views of the guidewire gripper of FIGS. 16A-16B.
Figure 17B:
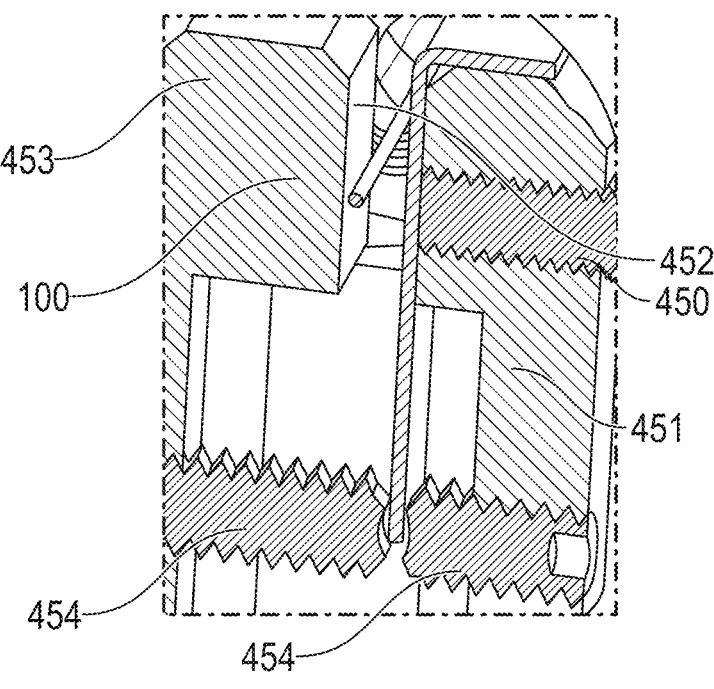
Figure 17C:
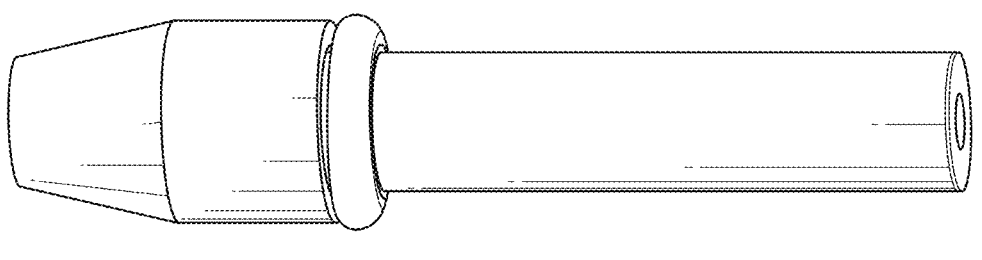
FIGS. 17C and 18B-18I are view of further implementations of a grippers in accordance with the present disclosure.

With reference to FIGS. 17A-17B, a cross section of the arm 430 of the gripper 400 is illustrated. The grip plate 452, made from plastic or metal (e.g., NiTi alloy) is fitted into the groove defined through the arm 430. The clamp 450 includes a rotatable screw threadably received within block 451 that, when rotated, pushes the plate 452 into the groove and pins the guidewire 100 against an opposing wall formed by block 453 that defines the groove. Screws 454 can be used to hold plate 452 in place. The movement of grip plate 452 as illustrated then is a cantilevered movement into the gap due to advancement of screw 450, and bending occurs about the clamped connection formed by screws 454. FIG. 17C depicts a further implementation of a wire gripper having a proximal handle portion with a grip, and a distal rotatable coupling that can couple to and hold a proximal end of a guide catheter in place, as well include one or more internal retainers to help hold a guidewire in place with respect to the guide catheter.

The disclosure further provides a kinker to kink and denude the core wire in the central region of the radiopaque marker pattern.

Figure 18A:
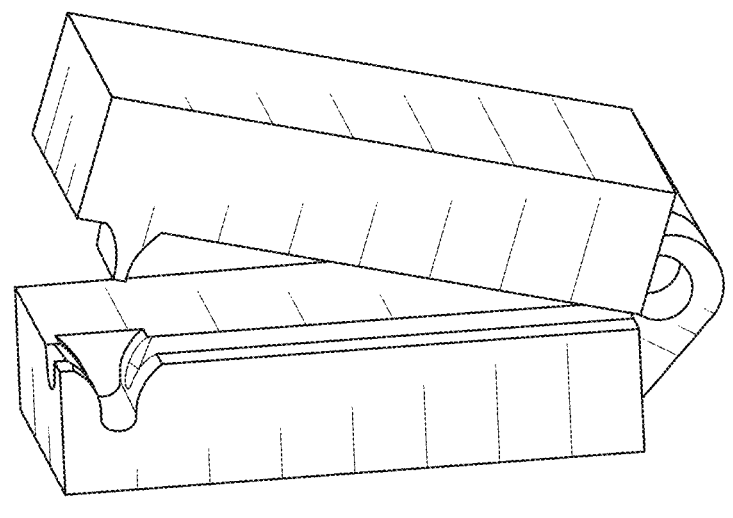
FIGS. 18A and 18J-18X are views of further implementations of kinker/denuders in accordance with the present disclosure.
Figure 18B:
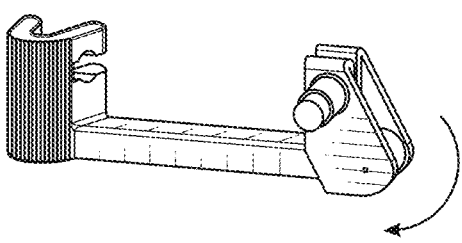
Figure 18C:
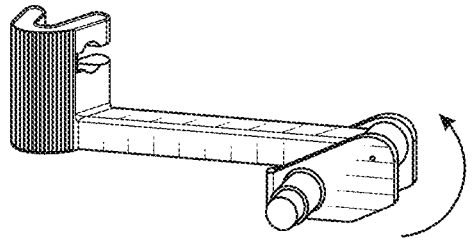
Figure 18D:
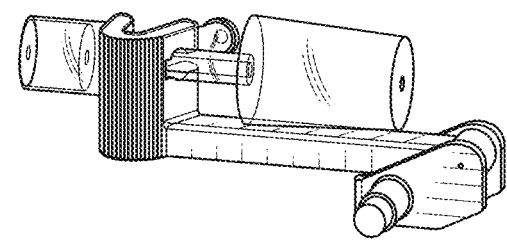
Figure 18E:
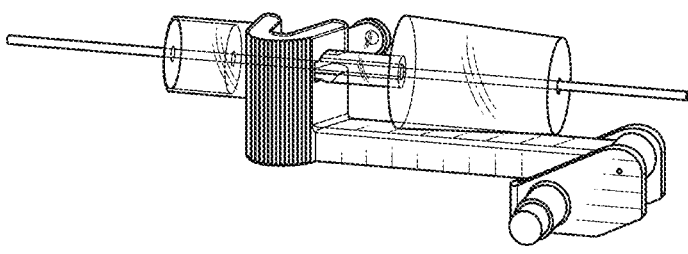
Figure 18F:
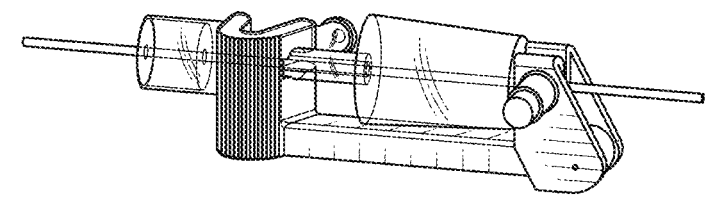
Figure 18G:
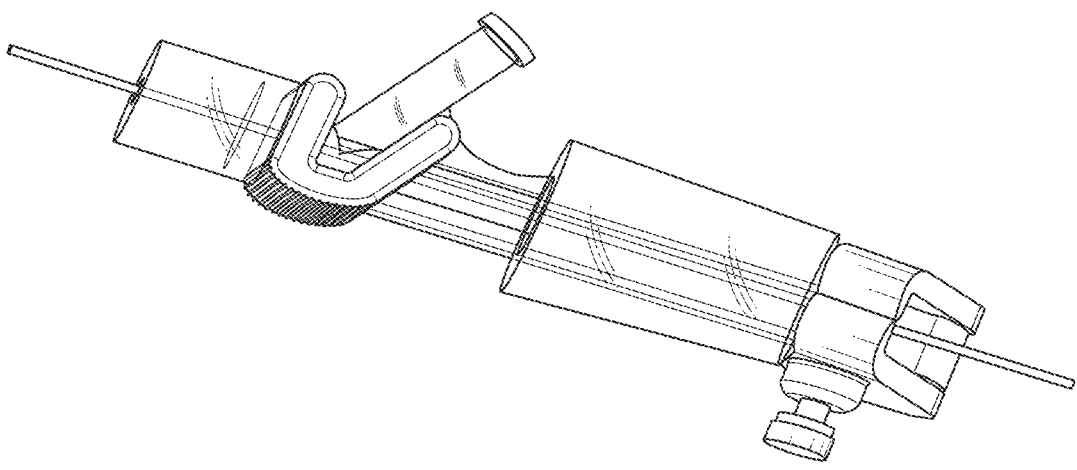

A first representative implementation of a kinker block that can be used to kink a guidewire as set forth herein can be seen in FIG. 18A. As depicted, the kinker block includes a first portion and a second portion joined by a pivoting connection at one end to permit the kinker block to open and close. A first, lower portion of the kinker block defines a channel or groove 1802 along its length to accommodate a guidewire to be kinked. The groove includes and is coincident with a "U" or a "V" shaped depression that is configured to receive a corresponding protrusion of the upper kinker block portion. In use, the guidewire is inserted into the groove or channel on the lower portion of the block when the upper portion of the block is pivoted out of the way from the lower portion of the block. The kinker block is then closed, and the protrusion fits into the corresponding depression, bending the guidewire in the process to form a kink therein. The protrusion can be further provided with one or more sharp edges to denude the insulation from the concave, inward portion of the kink that is formed on the guidewire.

Figure 18H:
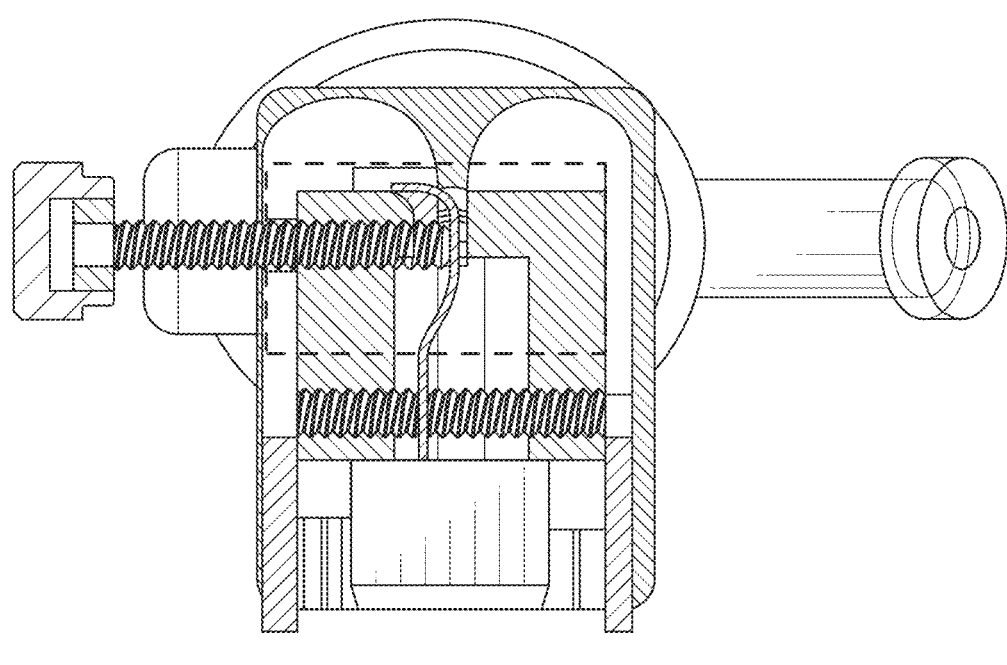
Figure 18I:
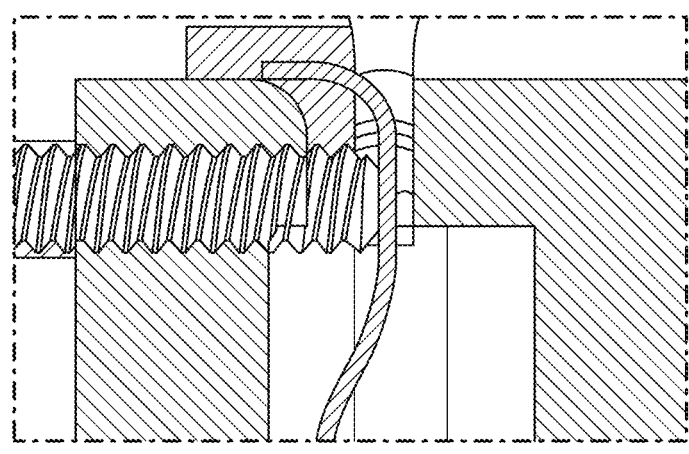
Figure 18J:
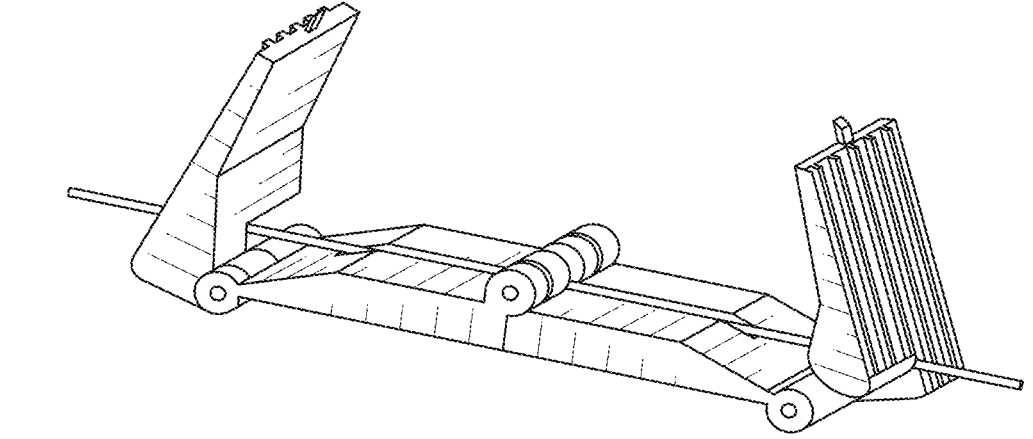
Figure 18K:
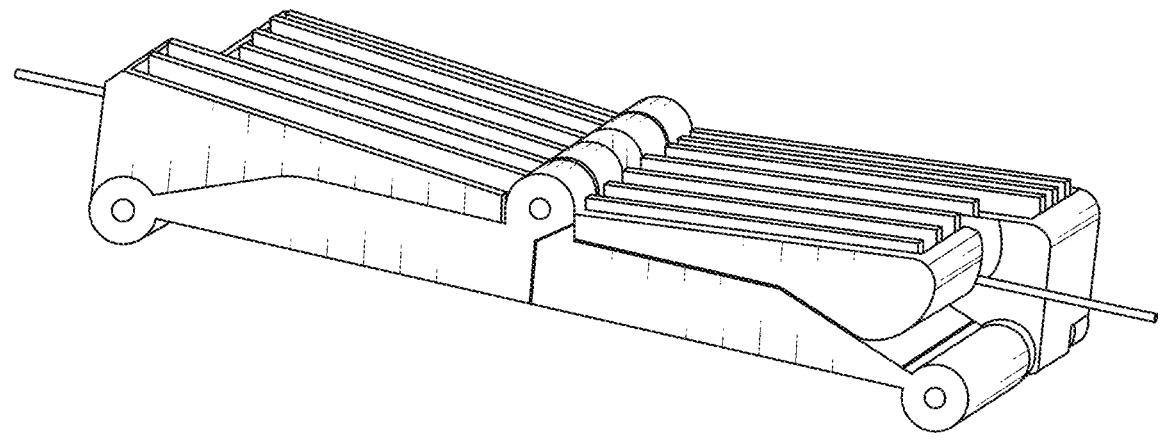
FIG. 18 is an isometric view of a guidewire kinker and denuder in accordance with the present disclosure in an open position to receive a guidewire to be denuded and kinked.
Figures 18L, 18M, 18N:
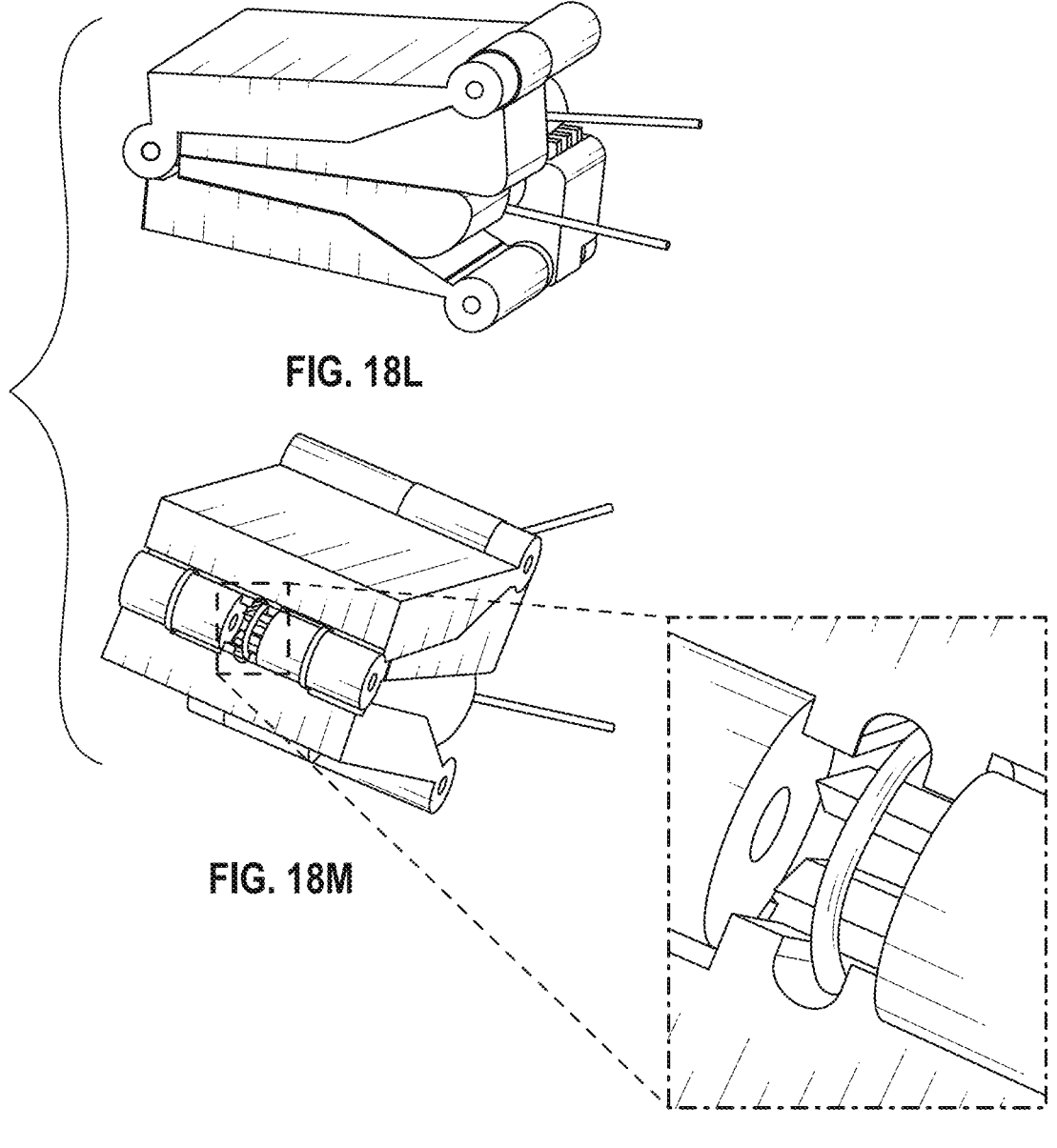

FIGS. 18B to 18I depict a further implementation of a guidewire gripper that can be used with a Y-Adapter, such as a typical off the shelf Y-Adapter. The guidewire gripper includes an elongate frame or body, illustrated as a rod or shaft. A first end of the gripper includes at least one gripping arm to hold a neck portion of a Y-Adapter in place. The at least one gripping arm is set forth as a flange located at the first end of the gripper that extends laterally outwardly from the main shaft or frame of the gripper and defines a pair of gripping arms. A second end of the frame includes a wire clamp pivotally attached thereto that rotates about a hinge ping that passes through the second end of the frame. In use, the gripping arms of the gripper snap over a neck portion of a Y-adapter (Step 1, FIG. 18D). The guidewire is then inserted through the Y-adapter (Step 2, FIG. 18E). The wire clamp at the second ("proximal") end of the frame is then rotated up (FIG. 18F) to cause the guidewire to fall into a channel of the clamp of the gripper as illustrated in the cross-sectional views (FIGS. 18H-18I). The manual screw can then be advanced into the channel of the clamp to clamp the guidewire in place between a distal face of the screw and a further portion of the clamp, such as a grip plate.

FIGS. 18J-18N illustrates a further kinker or denuder to remove a coating from a guidewire, typically a dielectric coating such as PTFE. The denuder includes two central frame portions joined at a central hinge that, when unfolded into an elongate configuration, defines an elongate wire channel along an upper side of the two central frame portions. Each central frame portion includes a further hinge at an outer end of the central frame portions that are connected by way of a hinge pin to a respective articulating arm that is connected to a respective central frame portion at a first end, and that includes a blade at a second free end thereof. As illustrated, the guidewire is introduced into the elongate channel defined along an upper face of the two central frame portions, the guidewire passing between two hinge bosses at a center of the kinker/denuder. The wire passes along a first lateral side of a first articulating arm, and a second opposing side of the second articulating arm as illustrated in the open position. The kinker/denuder is then closed first by collapsing each articulating arm toward its respective central frame portion. This places the kinker/denuder into the illustrated "closed position". The kinker/denuder is then folded again about its central hinge to collapse it and to bend the guidewire over onto itself at an acute angle. During this folding process, the guidewire contacts the denuder blades and scrapes the coating from the inside surface of the guidewire and, if so configured, can add a bend, or a kink to the guidewire.

Still a further implementation of a kinker block and wire denuder is depicted in FIGS. 18O-18X. The kinker block includes a main horizontal body portion coupled at either end by a pin to an upright pivoting arm, wherein each pivoting arm terminates in a pivoting knuckle that in turn includes a blade. The wire is laid in a groove per FIG. 18P and placed in a clamp that is parallel to the horizontal body portion. Per FIG. 18Q, the blades pivot toward the wire loaded into the groove and clamps, wherein the blades contact the wire at an outer edge of the denuding region (FIG. 18R). The blades begin moving toward the center as pressure is continued to be applied to the outer top sections (FIG. 18S). The blades then meet in the center and pressure is then directed downward to initiate formation of a kink in the wire (FIG. 18T). FIGS. 18U-18W illustrate the kinking process and FIG. 18X illustrates the kinked denuded wire in the kinker after the operation is completed.

For purposes of illustration, and not limitation, FIGS. 19A-24 illustrate aspects of still a further representative implementation of a kinker device 700 in accordance with the disclosure that is configured to controllably denude a portion of the core wire 115 of the guidewire 100. The kinker 700 can include a first arm, such as a first handle 730 and a second arm 720, such as a second handle, joined at a rotatable hinge including an axle 748 and a corresponding journal. The kinker 700 can be configured to hold the electrosurgical guidewire 100 in place with respect to the first arm 730 and second arm 720 to permit the electrosurgical guidewire 100 to be kinked when the first arm and second arm are folded at the rotatable hinge.

Figure 19A:
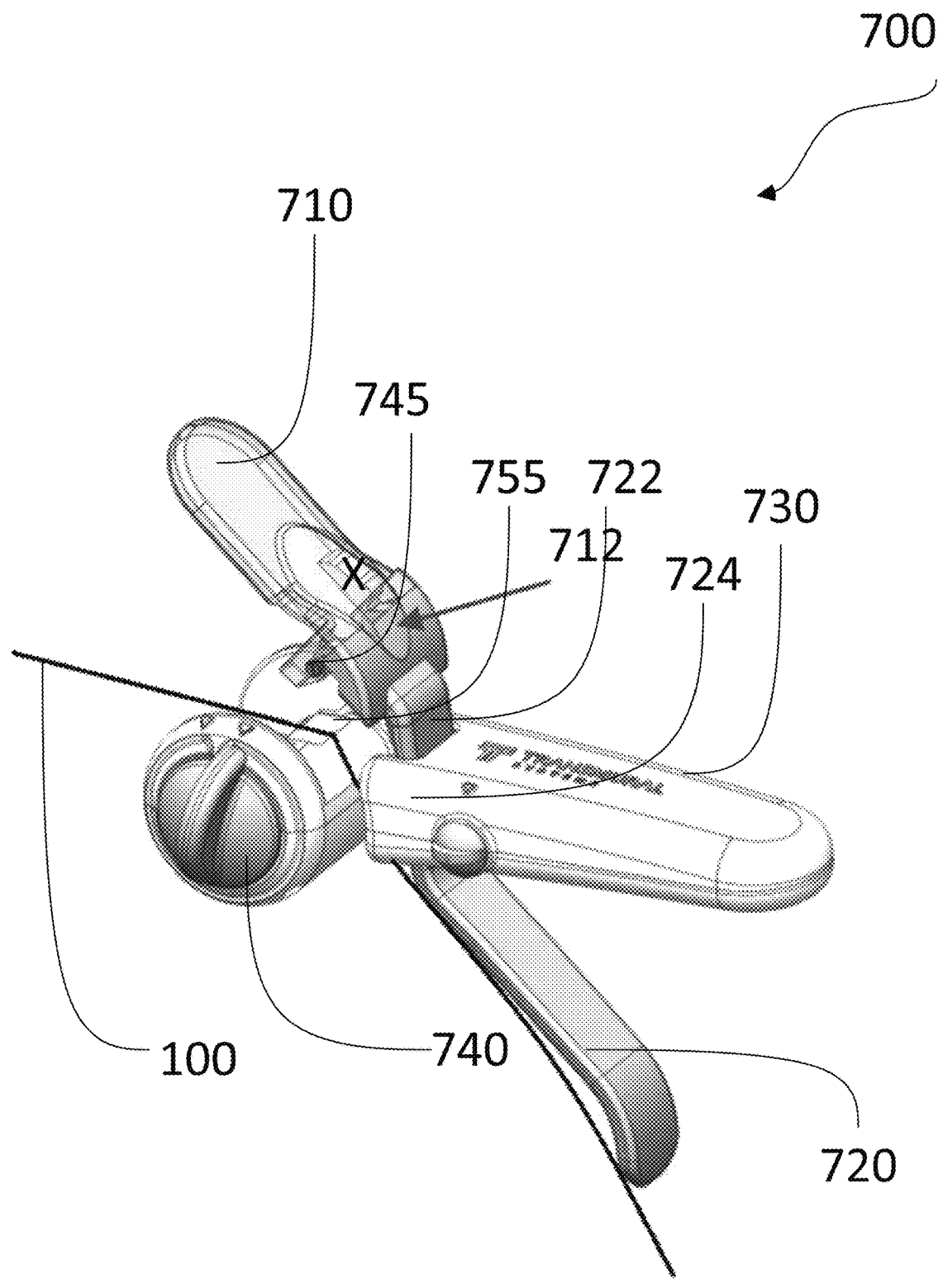
FIGS. 19A-19C are exploded views of a kinker showing upper and lower housing portions and a rotatable cutter held in place by the housing portions, and omitting a central lever of the kinker of FIGS. 20A-20B for purposes of clarity.
Figures 19B, 19C:
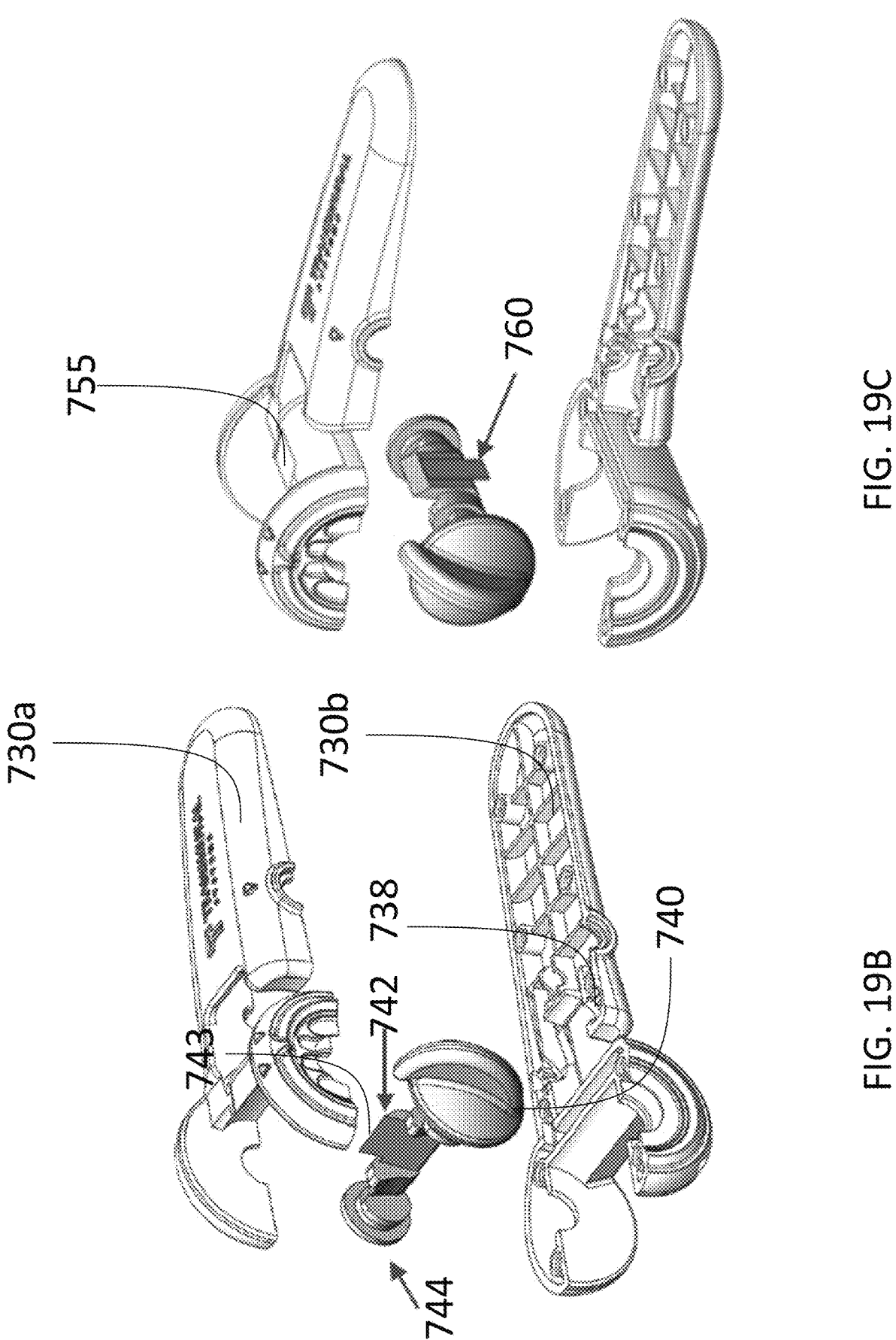
Figures 20A, 20B:
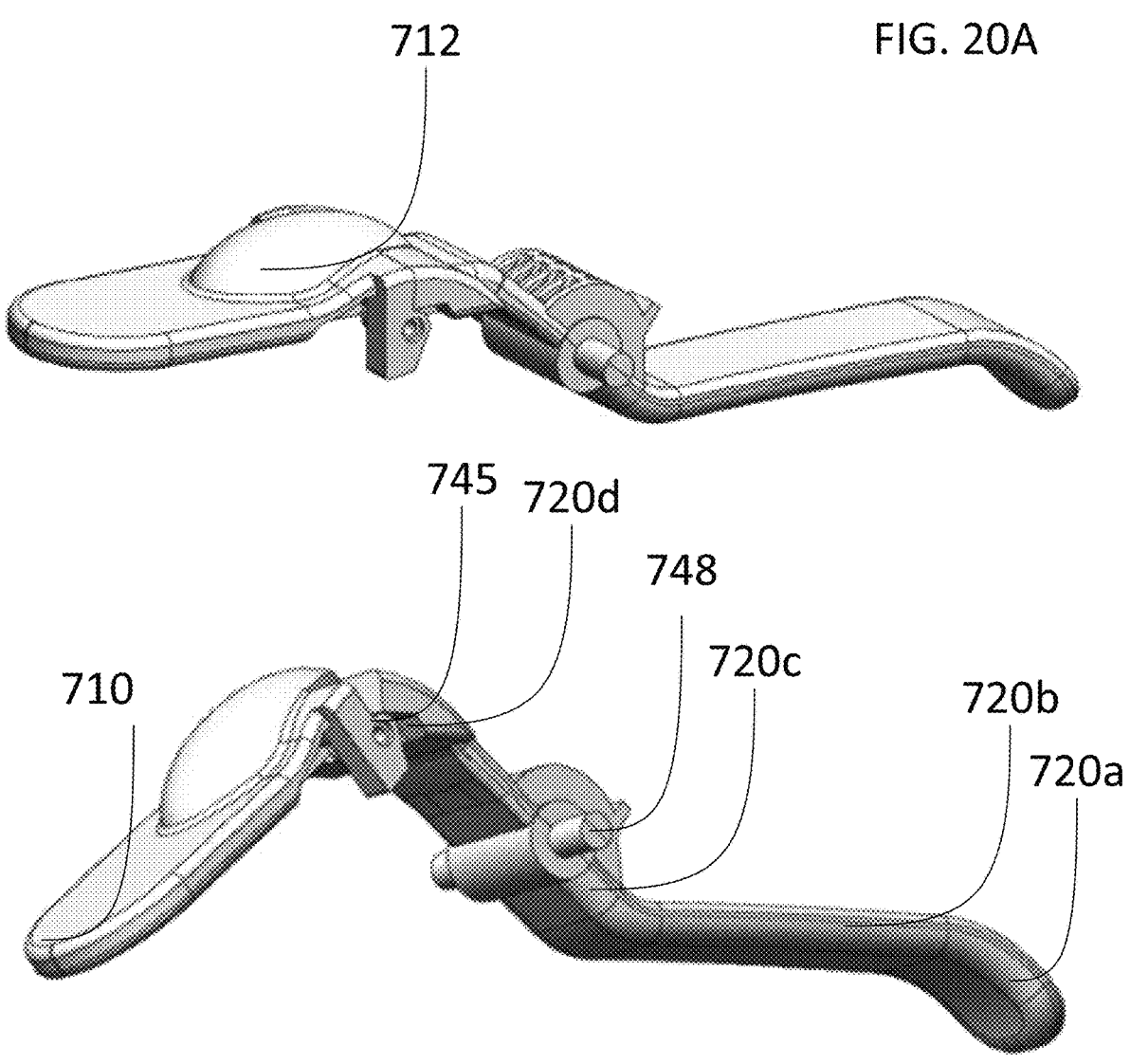
FIGS. 20A-20B are isometric views of a central lever of the kinker device of FIG. 18.

With reference to FIGS. 19A-20, the kinker 700 includes an elongate handle 730 that forms a main body of the device. A distal end of the handle 730 terminates in a rotatable joint that houses a rotating cutter 740. As shown in FIGS. 19B-19C, the handle 730 is formed from an upper portion 730a and a lower portion 730b, which cooperate to surround bearings formed into the cutter 740 such that the cutter 740 is rotatably disposed in the handle between a beginning position illustrated in FIG. 22A, and an end position illustrated in FIGS. 23A, 24A and 25A. The kinker 700 also includes a lever assembly 720 (FIGS. 20A-20B) that is rotatably received between the housing portions 730a, 730b.

In particular, a fulcrum, or bearing 748 is rotatably received in a journal 738 formed into the housing portions 730*a*, 730*b*. Lever assembly 720 includes a first handle portion that is pulled against the housing 730 when it is squeezed by a user. The handle portion begins at a proximal rounded end 720*a* that bends into a straight section 720*b* along a distal direction. The straight section 720*b* then bends to form an inclined, straight section 720*c* that includes bearing 748, which includes two axle ends. Section 720*c* then extends to a distal end 720*d* that includes a hinge point 745.

Flap or tab 710, including a window 712 that may have a lens element, is hingedly connected at hinge point 745. As discussed below, after the wire 100 is denuded, the flap or tab 710 is folded over to kink the guidewire within the kinker 700. As illustrated in FIG. 18, window 712 may be included with indicia X for aligning a guidewire 100 with platform 755 defined on the main body 730 of the device 700. Indicia X can also be provided, such as in the form of alignment markings or lines, on surface 755. Window 712, as depicted, includes a magnifying lens to indicate when the guidewire 100 has been properly aligned with the kinker 700. With reference to FIG. 19A-B, the cutter 740 includes two ends having arcuate bearing surfaces that are rotatably supported by corresponding journals formed into the main body 730. A central portion of the cutter includes a plate portion 742 that has a cutting blade 760 mounted thereon and a posterior edge 743 that the guidewire 100 is bent over (FIG. 25).

The tab 710 can be made, for example, from polycarbonate with a curved surface in the lens region 712 to visually magnify the wire. Markers can be provided on the bottom surface of the tab 710 to help a physician to align the guidewire.

The cutting blade 760 has an exposed cutting edge that sweeps out an arcuate path as the cutter 740 is rotated, wherein the clearance between the cutting edge and the guidewire is such that the cutting edge scrapes off material as the cutter handle is rotated.

Figure 22A:
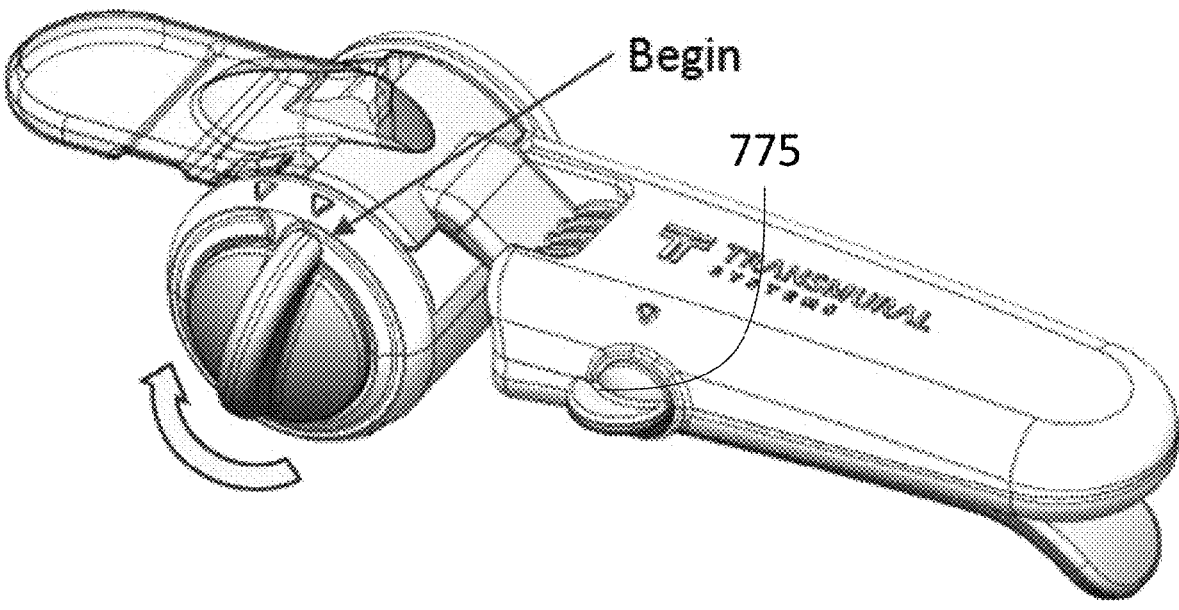
FIG. 22A is an isometric view of the device of FIG. 18 locked in place to denude and kink a guidewire.
Figure 22B:
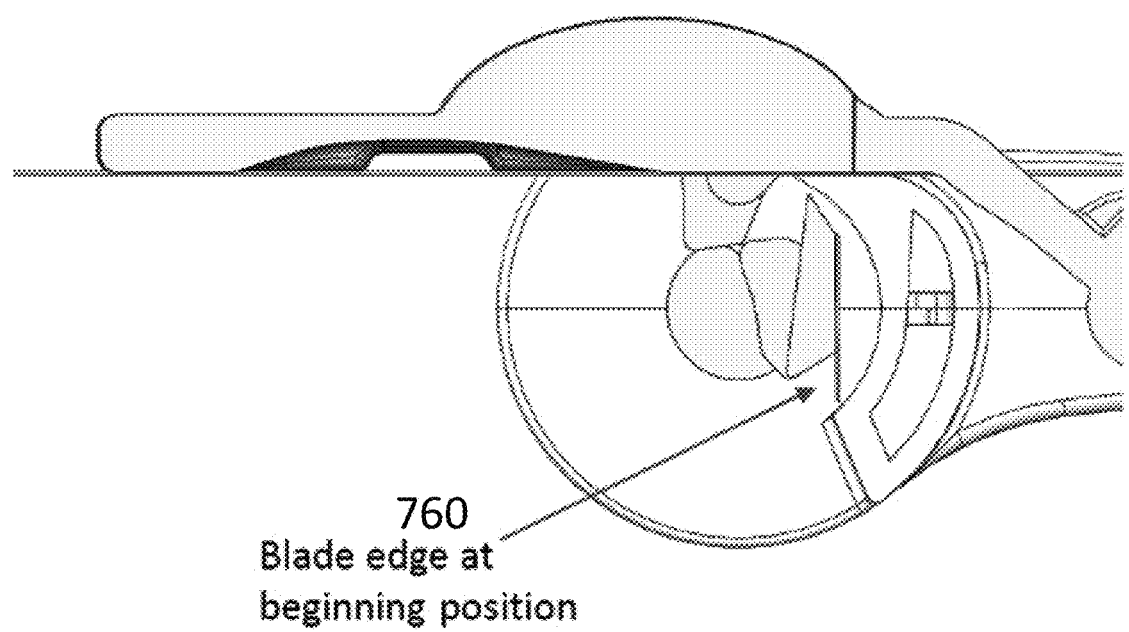
FIG. 22B is a cross sectional view of the device of FIG. 18 wherein the guidewire is about to be denuded with the blade in a starting position.

As illustrated in FIGS. 22A-B, at a starting position, the cutting blade is protected by a portion of the housing and cannot contact the guidewire. At this point, a physician aligns the gold markers to indicia or marks on the top tab, for example. The handle 720 can then be squeezed against handle 730 to engage the spring lock 775 in the handle 730.

FIGS. 22B, 23B, 24B and 25B illustrate cross sections of the device in the same orientation of the device as presented in FIGS. 22A, 23A, 24A and 25A, respectively. FIGS. 23A-23B show the cutter 740 rotated through a portion of its range of motion until it has just scraped the guidewire 100. During the motion, up to this point, the blade 760 scrapes across the guidewire 100. FIGS. 24A-24B show the blade in the end position where it once again is safely guarded from the guidewire.

With reference to FIGS. 25A-25B, when the knob is fully turned to the end position, the back of the blade 760, edge 743, is positioned such that the wire can be kinked over edge 743. At this time, tab 710 can be folded down about hinge 745, and the guidewire 100 is bent or kinked at the correct angle, after denuding is complete, to permit the electrosurgical procedure to be performed. The handle 720/730 can be squeezed a second time to release the spring lock 775 and open the handle to permit the kinked guidewire 100 to be removed.

Figures 21A, 21B:
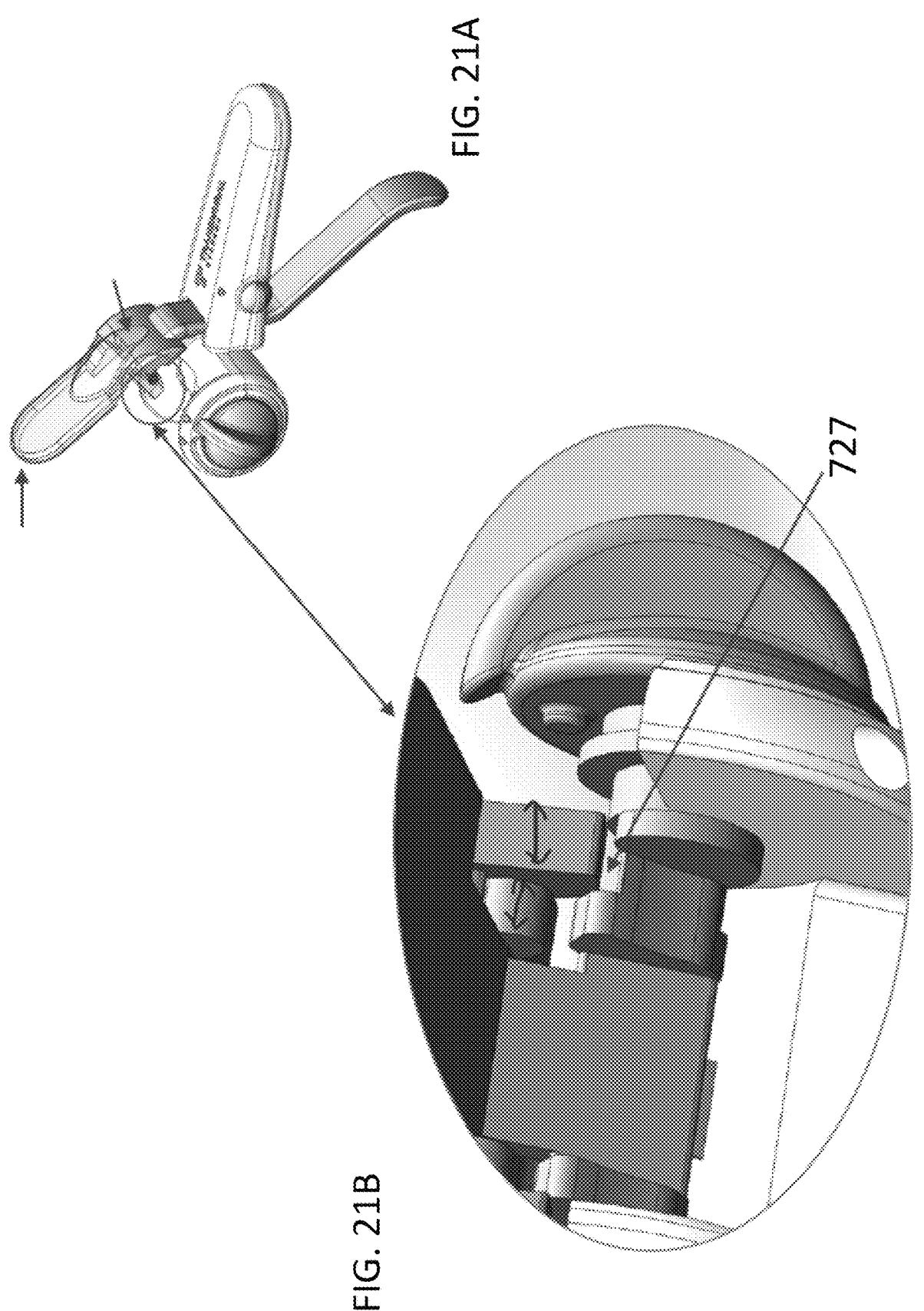
FIGS. 21A-21B depict a close up view of a portion of the kinker of FIG. 18.

FIG. 21A-B shows an enlarged view underneath the kinker 700 when it is in an open position to receive the guidewire 100. As can be seen, a notch 727 is defined in the axle of the rotating cutter 740 to permit the flap 710 of the handle assembly 720 to fold down when the cutter blade 760 is in the stowed final position as set forth in FIG. 24B, and prevents the flap or tab 710 from being folded before the cutter 740 is in the final, or end position. This is a kinker lock out mechanism that prevents kinking of the guidewire 100 prior to denuding. With reference to FIG. 22A, a spring loaded lock having an actuator 775 is received in the handle to hold the handle 720 in place against the handle 730, and to hold the guidewire in place between a lower surface of the flap and the surface 755 of the main body or handle 730.

FIGS. 26A-26G illustrate aspects of a further representative embodiment of a gripper device in accordance with the present disclosure. This implementation of the kinker/denuder operates in the same manner and has substantially the same components as the previous embodiment, with several differences. As with the prior embodiment, the kinker includes an elongate handle that forms a main body of the device. A distal end of the handle terminates in a rotatable joint that houses a rotating cutter as with the previous embodiment. The handle is similarly formed from an upper portion and a lower portion, which cooperate to surround bearings formed into the cutter such that the cutter is rotatably disposed in the handle between a beginning position similar to that illustrated in FIG. 22A, and an end position similar to that illustrated in FIGS. 23A, 24A and 25A. The kinker also includes a lever assembly that is rotatably received between the housing portions. In particular, a fulcrum, or bearing is rotatably received in a journal formed into the housing portions. The lever assembly includes a first handle portion that is pulled against the housing when it is squeezed by a user. The lever of this further embodiment is shorter than the prior embodiment to help facilitate one hand operation of the device. A detailed view of the lever assembly can be seen in FIGS. 26C, 26D, and 26E. A target location for a user's thumb, in the form of an oval shaped grip, is provided to help facilitate proper digit alignment. The handle similarly ends in a hinge point to pivotally receive a respective flap or tab 710, including a window that may have a lens element. After the wire is denuded, the flap or tab is folded over to kink the guidewire within the kinker. The window may be included with indicia for aligning a guidewire with the platform defined on the main body of the device.

With reference to FIGS. 26A, 26B, 26F, and 26G, a spring loaded lock having an actuator, similar to actuator 775 in the previous embodiment, is received in the handle to hold the handles in place and to hold the guidewire in place between a lower surface of the flap and the surface of the main body or handle. The handles can be squeezed together to lock the mechanism, and the lever of the actuator can be flicked with a user's finger of their hand that is gripping the device to cause the spring loaded lock to release to cause the arm and handle to pivot and separate, thereby permitting the kinked, denuded guidewire to be removed from the device.

In further accordance with the disclosure, a kit is provided to perform an electrosurgical procedure, including a guidewire as set forth herein, catheters as set forth herein, and, grippers as set forth herein, and a kinker and denuder to kink and denude the core wire in the central region of the radiopaque marker pattern. It will be appreciated that any of the illustrated embodiments can be used to form such a kit.

Methods of performing a valve leaflet cutting procedure are also set forth herein. The disclosed system can be used to accomplish any of the methods set forth in U.S. patent application Ser. No. 16/954,710, which is incorporated herein in its entirety for any purpose.

An illustrative method includes coupling a proximal end (e.g., 102) of an electrosurgical guidewire as set forth herein to an electrosurgical generator, directing a distal end of the electrosurgical guidewire (e.g., 104) into the patient's vasculature through a catheter to a valve leaflet to be cut, energizing the electrosurgical generator (e.g., 800) to energize the distal exposed end of the electrosurgical guidewire, and burning the valve leaflet tissue to form an opening therethrough. The method can further include advancing the electrosurgical guidewire through the valve leaflet, capturing the distal end of the electrosurgical guidewire with a snare catheter. An example of this method step is presented below with respect to an aortic valve, wherein a snare catheter (e.g., a catheter such as 280 bent into a shape resembling 300, 350 with a snare 320 or separate snare catheter inside) is directed through a patient's vasculature to capture the distal end 104 of the guidewire 100 that is delivered using a delivery catheter (e.g., 200, 250), and pulling the distal end 104 of the guidewire 100 out of the patient to externalize it alongside a proximal region of the electrosurgical guidewire. At this point, the guidewire 100, which is typically about 300 cm in length, is directed into the patient through catheter 200/250, and out through catheter 300/350, and passes through a valve leaflet.

At this point, the radiopaque marker region 110 of the guidewire is still outside the patient and has not yet been introduced. The guidewire can then be kinked and denuded using the kinker 700, while outside of the patient. The kinked portion of the guidewire 100 can then be advanced into the patient's anatomy until the kinked portion of the guidewire straddles the opening burned in the valve leaflet. At this point, the grippers 400 may be attached to the catheter proximal ends to build the system of FIG. 15, which can also include reservoirs or syringes 500 including dextrose solution coupled to the Y-connector 440 of each respective gripper to inject fluid through the catheters as needed to the tissue cutting site.

With reference to FIGS. 13 and 14, the denuded kinked portion 110b/110c of the guidewire, which now straddles the valve leaflet (not shown) can be used to form an electrosurgical instrument in cooperation with the catheters. This can be done under fluoroscopy by viewing the gold marker bands, as well as one or more radiopaque markers located at the distal ends 284 of the catheters 280. The bands 114a-f, which have a known physical separation, and the catheter distal ends 284 can be moved close enough to the cutting area to support the cutting, but not so close as to get melted or damaged by the electrosurgical cutting procedure. Thus, an assembly, or system, is constructed for performing an electrosurgical procedure, and it may be assembled with reference to the markings 114a-f to ensure that the tips 284 of the catheters 280 are a predetermined distance from the cutting area.

In some implementations, the valve leaflet can be punctured at a position located radially inwardly from a valve annulus. This is sometimes needed to as to avoid the need for puncturing the valve leaflet too close to the valve annulus where calcified deposits may have accumulated. Once the leaflet has been so punctured by a guidewire as set forth herein, a catheter including an inflatable member, such as a balloon, or other expansible catheter can be introduced over the guidewire and introduced through the hole in the leaflet, for example, through the annular space defined between catheter 200 and the guidewire 100. The inflatable member can then be expanded to enlarge the opening in the leaflet at least partially along a radially outward direction toward the valve annulus.

Whether or not the opening is enlarged as described above, distal tips 284 of each catheter 280 can be advanced under visualization to a location proximal to the kinked denuded region of the guidewire, and indicia 114a-f on the guidewire can be used to maintain a predetermined spacing between the guiding catheters and the kinked denuded region of the guidewire to prevent damage to the guiding catheters. The method can further include activating the electrosurgical power source 800, and burning through the tissue of the valve leaflet using the kinked denuded portion 110b of the guidewire 100 to complete a cut through the valve leaflet, preferably while flushing at the same time with dextrose solution.

Figure 12:
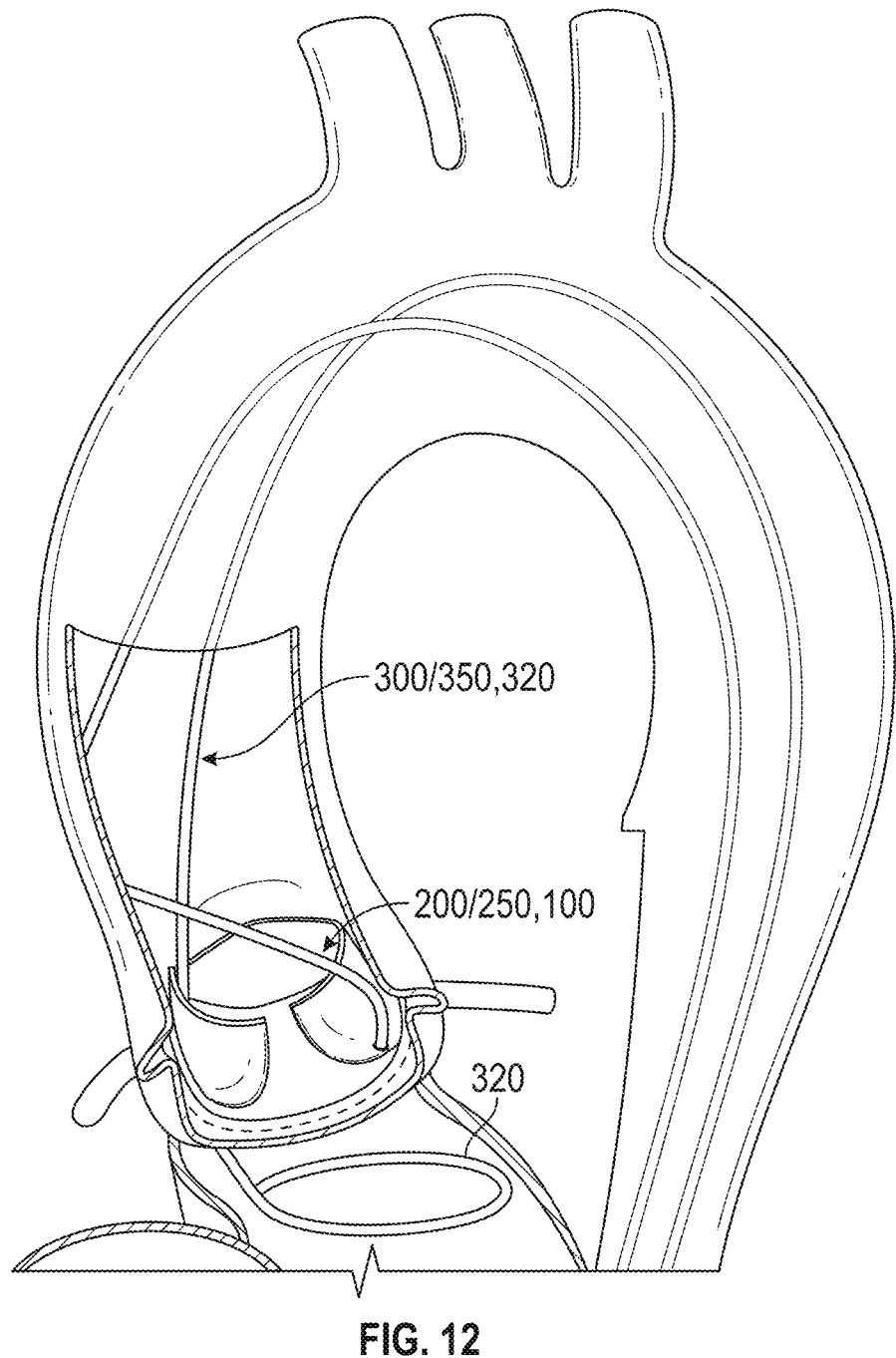
FIG. 12 is an illustration of relative placement of a snare catheter in accordance with the present disclosure and a catheter that delivers a guidewire.

With reference to FIGS. 10-11, a catheter having the general layout of catheter 280 can be shaped as a guiding or snare catheter 300 (e.g., JR 4.0 catheter), or 350 (e.g., multi-purpose catheter), as appropriate. The catheter 280 can simply be shaped accordingly, and a separate snare or snare catheter can be introduced along its length. Regardless, a catheter is selected with an appropriate shape and durometer profile to best traverse the tortious anatomy of the patient's luminal system, depending on the structure being worked on. Examples of suitable snare catheters can be found, for example, in U.S. patent application Ser. No. 13/824,198, filed May 1, 2013, which is expressly incorporated by reference herein for any purpose whatsoever). The snare 320 of the snare catheter can be directed out of the distal end of the selected snare catheter 300/350 (FIG. 12) to provide a landing or target zone for a guidewire 100 that is directed through the distal end of the selected delivery or crossing catheter 200/250. This permits a guidewire 100 that traverses through the distal end of the catheter 200/250 to be captured by the snare 320 of the snare catheter 300/350 thereby permitting the guidewire to be pulled into the distal end of the catheter 300/350, and advanced therethrough and externalized. As set forth in FIG. 12, the crossing catheter 200/250 and the snaring catheter 300/350 are in place to support left leaflet laceration.

The disclosure also provides an electrosurgical system including a radio frequency power supply (such as that described in U.S. Pat. No. 6,296,636, which is incorporated by reference herein in its entirety for any purpose whatsoever) operably coupled to the electrically conductive core wire 115. Thus, the radio frequency power supply can be operably (and selectively) coupled to the electrically conductive core wire and to the second electrical conductor, as desired by way of a cable 600. Any suitable power level and duty cycle can be used in accordance with the disclosed embodiments. For example, continuous duty cycle (cutting) radiofrequency ("RF") energy can be used, for example, at a power level between about 10 and 30 or 50 Watts, for example, or any increment therebetween of about one watt. The cuts can be made by applying power for between about one half of a second and about five seconds, or any increment therebetween of about one tenth of a second. The electrosurgery generator can be the Medtronic Force FX C Generator that achieves 5 W to 300 Watts of monopolar radiofrequency (RF) energy, for example.

Each of the guiding catheters can be made from a variety of materials, including multilayer polymeric extrusions, such as those described in U.S. Pat. No. 6,464,683 to Samuelson or U.S. Pat. No. 5,538,510 to Fontirroche, the disclosure of each being incorporated by reference herein in its entirety. Other structures are also possible, including single or multilayer tubes reinforced by braiding, such as metallic braiding material. Any of the catheters or guidewires disclosed herein or portions thereof can be provided with regions of varying or stepped-down stiffness with length using any of the techniques set forth in U.S. Pat. No. 7,785,318, which is incorporated by reference herein in its entirety for any purpose whatsoever.

The catheters disclosed herein can have a varied stiffness along their length, particularly in their distal regions by adjusting the cross-sectional dimensions of the material to impact stiffness and flexibility, while maintaining pushability, as well as the durometer of the material. Hardness/stiffness is described herein with reference to Shore hardness durometer ("D") values. Shore hardness is measured with an apparatus known as a Durometer and consequently is also known as "Durometer hardness". The hardness value is determined by the penetration of the Durometer indenter foot into the sample. The ASTM test method designation is ASTM D2240 00. For example, in some implementations, a more proximal region of the catheter can have a durometer of about 72 D, an intermediate portion of the catheter (the proximal most 20-30 cm of the last 35 cm, for example that typically traverses an aortic arch) can have a durometer of about 55 D, and the distal 5-10 cm of the catheter can have a durometer of about 35 D.

Any surface of various components of the system described herein or portions thereof can be provided with one or more suitable lubricious coatings to facilitate procedures by reduction of frictional forces. Such coatings can include, for example, hydrophobic materials such as Poly-TetraFluoroEthylene ("PTFE") or silicone oil, or hydrophilic coatings such as Polyvinyl Pyrrolidone ("PVP"). Other coatings are also possible, including, echogenic materials, radiopaque materials and hydrogels, for example.

Implementations of the disclosed guidewires preferably include a sterile, single use device intended to cut soft tissue. References to dimensions and other specific information herein is intended to be illustrative and non-limiting. In one implementation, the disclosed guidewire has an outer diameter of 0.014" and a working length of 260-300 cm. The proximal end of the disclosed guidewire, which has no patient contact, can be un-insulated to allow for connection to an electrosurgery generator.

One application of the disclosed embodiments can be BASILICA (Bioprosthetic Aortic Scallop Intentional Laceration to prevent Iatrogenic Coronary Artery obstruction during transcatheter aortic valve replacement). The procedure is performed under general anesthesia or under moderate sedation at the discretion of the institutional heart team. The BASILICA procedure typically has three steps as described elsewhere in this patent application, including (i) leaflet traversal by cutting using the distal guidewire tip, followed by (ii) leaflet laceration by cutting using the guidewire mid-shaft lacerating surface, immediately followed by (iii) TAVR using marketed devices. These steps are all typically guided by fluoroscopy and adjunctive echocardiography as needed.

First, catheter access is obtained typically via multiple arterial introducer sheaths/guiding catheters as disclosed herein. In some variations, at various steps of the procedure, two or four catheters can be used for BASILICA (often with catheter pairs introduced side-by-side into single large-bore introducer sheaths), one for hemodynamics and angiography, and one for TAVR) and at least one venous introducer sheath for temporary transveous pacing. Anticoagulation with heparin or equivalent achieves an activated clotting time is typically 250-300 s. Cerebral embolic protection devices are employed at the discretion of the operator. Two retrograde catheters can be positioned, using a guidewire anchor as needed. Care is taken to avoid entrapment of mitral valvular structures. A snare catheter is positioned. A traversal guiding catheter directs the guidewire against the base of the coronary cusp targeted for laceration, using fluoroscopic and/or echocardiographic guidance. The kink in the guidewire self-orients the denuded lacerating surface with the leaflet tissue intended to be cut. Nonionic conductive flush (e.g., dextrose 5%) is administered as needed during electrosurgery via the guiding catheters to reduce non-target electrical pathways and to reduce guidewire char and thromboembolism. The BASILICA procedure may be performed on one or two valve leaflets that may threaten coronary artery obstruction.

Generally, cutting using the disclosed system can be performed by positioning the laceration (denuded mid-shaft) surface along the intended leaflet base, and applying traction on both free ends of the guidewire with the wire grippers 400 while simultaneously applying electrosurgery energy (typically 50-70 W) in short bursts, until the laceration is complete and the guidewire is free. The guidewire and BASILICA catheters are removed. With the leaflets cut, installation of a TAVR can then performed.

The text and figures of the Appendix of U.S. Patent Application No. 63/047,995, filed Jul. 3, 2020 are incorporated by reference herein for all purposes. The Appendix of U.S. Patent Application No. 63/077,579, filed Sep. 12, 2020 is incorporated by reference herein in its entirety for all purposes. FIGS. 31-34, 79-81 and 105-114 and related text of International Patent Application No. PCT/US2020/055160, filed Oct. 9, 2020 describing a guidewire, kinker block and related hardware are all incorporated by reference herein for all purposes.

The devices and methods disclosed herein can be used for other procedures in an as-is condition, or can be modified as needed to suit the particular procedure. This procedure for cutting the leaflet can be used in support of a variety of procedures where it is useful to cut a valve leaflet. For example, it can be very useful to perform such a cutting procedure for clearing space for a replacement valve, such as a replacement, mitral or tricuspid valve. The valve leaflets can be cut accordingly making space for a replacement valve to be installed in any desired manner. Likewise, while it can be appreciated that a monopolar cutting system is disclosed, in certain implementations, it is also possible to configure the system to operate in a bipolar configuration. During the step of leaflet laceration, the system can be configured to deliver energy to the leaflet with electrosurgical pads coupled to the patient to complete the circuit. When lacerating the leaflet or other structure with the bent denuded cutting wire, most of the energy is still dissipated in the patient.

In view of the many possible embodiments to which the principles of this disclosure may be applied, it should be recognized that the illustrated embodiments are only preferred examples of the disclosure and should not be taken as limiting the scope of the disclosure. Each and every patent and patent application referenced herein is expressly incorporated by reference herein in its entirety for any purpose whatsoever.

What is claimed is:

1. A kit for performing an electrosurgical procedure comprising:
   an electrosurgical guidewire including:
      a core wire having a proximal end, and a distal end and being defined by an outer surface between the proximal end and the distal end of the core wire, said core wire having a centerline that traverses the length of the core wire from the proximal end to the distal end of the core wire;

a dielectric coating disposed about the core wire, wherein the proximal end and distal end of the core wire are electrically exposed and the proximal end of the core wire is configured to be coupled to an electrosurgical generator;

a radiopaque marker pattern disposed over the core wire to indicate a location proximate a middle section of the guidewire to be kinked and partially denuded by removing the dielectric coating to electrically expose the core wire; and a pair of guiding catheters, each said guiding catheter having a proximal end and a distal end and defining an elongate lumen along its length, wherein a distal opening defined in each guiding catheter is configured to receive the proximal end of the core wire therethrough or the distal end of the core wire therethrough;

a pair of grippers, each said gripper being configured to be coupled to a respective proximal end of each said guiding catheter, wherein each said gripper is further configured to be selectively coupled to the guidewire to permit the relative position of the guidewire and the guiding catheters to be fixed; and a kinking and denuding device that is configured to kink and denude the core wire proximate the radiopaque marker.

2. The kit of claim 1, wherein the kinking and denuding device includes a first arm and a second arm joined at a rotatable hinge, wherein the kinking and denuding device is configured to hold the electrosurgical guidewire in place with respect to the first arm and second arm to permit the electrosurgical guidewire to be kinked when the first arm and second arm are folded at the rotatable hinge.

3. The kit of claim 1, wherein the kinking and denuding device includes visual indicia thereon to provide alignment with the radiopaque marker of the electrosurgical guidewire.

4. The kit of claim 1, wherein the kinking and denuding device includes an optical lens to magnify the radiopaque marker of the electrosurgical guidewire.

5. The kit of claim 1, wherein the kinking and denuding device includes a rotatably mounted blade configured to be rotated about a central axis, wherein successive revolutions of the rotatably mounted blade strip the dielectric coating from the electrosurgical guidewire.

6. A method of using the kit of claim 1 to perform a valve leaflet cutting procedure, comprising:

coupling a proximal end of the core wire to an electrosurgical generator;

directing the distal end of the core wire into the patient's vasculature to a valve leaflet to be cut;

energizing the electrosurgical generator to energize the distal electrically exposed end of the core wire;

burning an opening through tissue of the valve leaflet with the electrically energized distal end of the core wire;

advancing a portion of the electrosurgical guidewire through the opening formed through valve leaflet;

capturing the distal end of the electrosurgical guidewire with a snare catheter; and pulling the distal end of the guidewire out of the patient to externalize it alongside a proximal region of the electrosurgical guidewire.

7. The method of claim 6, further comprising forming a kink into the guidewire and denuding the radiopaque marker with the kinking and denuding device while the guidewire is located outside of the patient, and advancing the kinked, denuded portion of the guidewire into the patient's anatomy until the kinked portion of the guidewire is adjacent to the opening formed through the valve leaflet.

8. The method of claim 7, further comprising directing each of the guiding catheters over each portion of the externalized guidewire until the distal end of each guiding catheter is located proximate the valve leaflet.

9. The method of claim 8, further comprising using indicia formed onto the guidewire to maintain a predetermined spacing between the distal end of each said guiding catheter and the kinked denuded region of the guidewire to prevent electrical damage to the guiding catheters.

10. The method of claim 9, further comprising activating the electrosurgical power source, and burning through the tissue of the valve leaflet using the kinked denuded portion of the guidewire to complete a cut through the valve leaflet.

* * * * *